United States Patent
Copa et al.

(10) Patent No.: US 9,307,991 B2
(45) Date of Patent: *Apr. 12, 2016

(54) ANASTOMOSIS DEVICE AND RELATED METHODS

(75) Inventors: Vincent G. Copa, Minnetonka, MN (US); Kory P. Hamel, Bloomington, MN (US)

(73) Assignee: AMS Research, LLC, Minnetonka, MN (US)

( * ) Notice: Subject to any disclaimer, the term of this patent is extended or adjusted under 35 U.S.C. 154(b) by 2355 days.

This patent is subject to a terminal disclaimer.

(21) Appl. No.: 10/919,545

(22) Filed: Aug. 16, 2004

(65) Prior Publication Data

US 2005/0070938 A1    Mar. 31, 2005

Related U.S. Application Data

(63) Continuation-in-part of application No. 10/646,383, filed on Aug. 21, 2003, now Pat. No. 8,551,126.

(60) Provisional application No. 60/405,140, filed on Aug. 22, 2002.

(51) Int. Cl.
*A61B 17/08* (2006.01)
*A61B 17/11* (2006.01)

(52) U.S. Cl.
CPC .......... *A61B 17/11* (2013.01); *A61B 2017/1103* (2013.01); *A61B 2017/1139* (2013.01)

(58) Field of Classification Search
CPC ...................... A61B 17/11; A61B 2017/1103
USPC .............. 606/151; 600/29–31; 604/96.01, 22
See application file for complete search history.

(56) References Cited

U.S. PATENT DOCUMENTS

| | | |
|---|---|---|
| 4,701,162 A | 10/1987 | Rosenberg |
| 4,705,502 A | 11/1987 | Patel |
| 4,792,330 A | 12/1988 | Lazarus et al. |
| 4,848,367 A | 7/1989 | Avant et al. |
| 4,873,977 A | 10/1989 | Avant et al. |
| 4,909,785 A | 3/1990 | Burton et al. |
| 4,911,164 A | 3/1990 | Roth |
| 4,932,956 A | 6/1990 | Reddy et al. |
| 5,047,039 A | 9/1991 | Avant et al. |
| 5,123,908 A | 6/1992 | Chen |

(Continued)

FOREIGN PATENT DOCUMENTS

| | | |
|---|---|---|
| WO | WO 92/04869 | 4/1992 |
| WO | WO 96/07447 | 3/1996 |

(Continued)

OTHER PUBLICATIONS

Hruby, G. W., "Comparison of a Novel Tissue Apposing Device and Standard Anastomotic Technique for Vesicourethral Anastomoses," Journal of Endourology, vol. 20, Supplement 1, VP12-02, p. A69 (abstract) Aug. 2006.

(Continued)

*Primary Examiner* — Diane Yabut
(74) *Attorney, Agent, or Firm* — Bookoff McAndrews, PLLC

(57) ABSTRACT

Described are methods and devices relating to anastomosis procedures, including those that reconnect the urethra and bladder after a radical prostatectomy, wherein the devices incorporate tissue approximating structure to maintain contact between tissues for healing the tissues together.

17 Claims, 17 Drawing Sheets

(56) References Cited

U.S. PATENT DOCUMENTS

| | | | |
|---|---|---|---|
| 5,152,772 A | 10/1992 | Sewell, Jr. | |
| 5,306,226 A * | 4/1994 | Salama | 600/29 |
| 5,540,701 A * | 7/1996 | Sharkey et al. | 606/153 |
| 5,545,171 A | 8/1996 | Sharkey et al. | |
| 5,599,321 A * | 2/1997 | Conway et al. | 604/265 |
| 5,695,504 A | 12/1997 | Gifford, III et al. | |
| 5,707,380 A | 1/1998 | Hinchliffe et al. | |
| 5,833,698 A | 11/1998 | Hinchliffe et al. | |
| 5,931,842 A | 8/1999 | Goldsteen et al. | |
| 5,964,791 A | 10/1999 | Bolmsjo | |
| 6,024,748 A | 2/2000 | Manzo et al. | |
| 6,119,045 A | 9/2000 | Bolmsjo | |
| 6,149,667 A | 11/2000 | Hovland et al. | |
| 6,193,734 B1 | 2/2001 | Bolduc et al. | |
| 6,238,368 B1 | 5/2001 | Devonec | |
| 6,254,570 B1 | 7/2001 | Rutner et al. | |
| 6,299,598 B1 | 10/2001 | Bander | |
| 6,302,905 B1 | 10/2001 | Goldsteen et al. | |
| 6,391,039 B1 | 5/2002 | Nicholas et al. | |
| 6,416,545 B1 | 7/2002 | Mikus et al. | |
| 6,440,146 B2 | 8/2002 | Nicholas et al. | |
| 6,447,533 B1 | 9/2002 | Adams | |
| 6,461,367 B1 * | 10/2002 | Kirsch et al. | 606/144 |
| 6,485,496 B1 | 11/2002 | Suyker et al. | |
| 6,494,908 B1 | 12/2002 | Huxel et al. | |
| 6,520,974 B2 | 2/2003 | Tanner et al. | |
| 6,530,932 B1 | 3/2003 | Swayze et al. | |
| 6,562,024 B2 | 5/2003 | Alvarez de Toledo et al. | |
| 6,565,579 B2 | 5/2003 | Kirsch et al. | |
| 6,599,311 B1 * | 7/2003 | Biggs et al. | 606/232 |
| 6,602,243 B2 | 8/2003 | Noda | |
| 6,695,832 B2 | 2/2004 | Schon et al. | |
| 6,702,825 B2 | 3/2004 | Frazier et al. | |
| 6,719,709 B2 | 4/2004 | Whalen et al. | |
| 6,719,749 B1 | 4/2004 | Schweikert et al. | |
| 6,726,697 B2 | 4/2004 | Nicholas et al. | |
| 6,740,098 B2 | 5/2004 | Abrams et al. | |
| 6,746,456 B2 | 6/2004 | Xiao | |
| 6,746,472 B2 | 6/2004 | Frazier et al. | |
| 8,551,126 B2 * | 10/2013 | Copa et al. | 606/153 |
| 2001/0049492 A1 | 12/2001 | Frazier et al. | |
| 2002/0002363 A1 | 1/2002 | Urakawa et al. | |
| 2002/0087176 A1 | 7/2002 | Greenhalgh | |
| 2003/0069629 A1 | 4/2003 | Jadhav et al. | |
| 2003/0208183 A1 | 11/2003 | Whalen et al. | |
| 2003/0229364 A1 | 12/2003 | Seiba | |
| 2004/0078047 A1 | 4/2004 | Nicholas et al. | |
| 2005/0251155 A1 * | 11/2005 | Orban, III | 606/153 |

FOREIGN PATENT DOCUMENTS

| | | |
|---|---|---|
| WO | WO99/16359 | 4/1999 |
| WO | WO 99/21490 | 5/1999 |
| WO | WO 99/21491 | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034813 | 4/2004 |
| WO | WO 2004/034913 | 4/2004 |
| WO | 2007/013070 A1 | 2/2007 |

OTHER PUBLICATIONS

Hruby, G. W., "Comparison of a Novel Tissue Apposing Device and Standard Anastomotic Technique for Vesicourethral Anastomoses," The Journal of Urology, vol. 175, No. 4, p. 347, Apr. 2006.

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

ANASTOMOSIS DEVICE AND RELATED METHODS

CROSS REFERENCE TO RELATED APPLICATION

The present application is a continuation in part of U.S. Ser. No. 10/646,383, filed Aug. 21, 2003, now U.S. Pat. No. 8,551,126, which is the nonprovisional application claiming priority to Provisional Application Ser. No. 60/405,140, filed Aug. 22, 2002, the entire contents of each of which are fully incorporated herein by reference.

FIELD OF THE INVENTION

The invention relates to methods of performing anastomosis procedures as well as related devices.

BACKGROUND

Anastomosis procedures are required for connecting or re-connecting body tissue, e.g., as part of a surgical procedure. The tissue may be part of a body lumen such as a blood vessel, intestinal or other digestive system tissue, or tissue relating to the urinary system. As one example, in a radical prostatectomy, a surgeon removes all or most of a patient's prostate. Because the urethra travels through the prostate immediately before reaching the bladder, the upper part of the urethra is also removed with the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these or other anatomical bodies. Installation of sutures, however, with a needle, to connect severed tissues, can be a difficult and technique-sensitive task. Many factors can make the task difficult, including a very small amount of tissue to work with (e.g., at the urethral stump and at the bladder neck), and proximal sensitive tissues such as ureters at a bladder and a proximal nerve bundle and sphincter at a urethral stump. These factors result in complicated and delicate suturing procedures that, if not performed properly, could result in complications such as leakage, difficulty in healing or failure to heal, or specific conditions such as incontinence or impotence. Specific problems include necrosis of the sutured tissues; stricture of the urethra, which impedes the flow of fluid through the urethra; and a urethra-bladder connection that is not fluid-tight. In addition, methods of suturing the urethra to the bladder allow for accidental or inadvertent piercing of the nearby neurovascular bundle, which can cause incontinence or impotence.

SUMMARY

The invention relates to anastomosis devices, including, in specific embodiments, devices that include tissue approximating structure and a drainage feature. Anastomosis devices that include tissue approximating structure are described in Applicants' co-pending U.S. patent application Ser. No. 10/646,383, filed Aug. 21, 2003, entitled "ANASTOMOSIS DEVICE AND RELATED METHODS," as well as "ANASTOMOSIS DEVICE AND RELATED METHODS," AMS0008/US/2 filed on even date herewith, the entireties of both of which are incorporated herein by reference. These devices allow for methods of re-connecting tissue with the use of the tissue approximating structure.

Anastomosis devices that include tissue approximating structure can advantageously eliminate the need for sutures to reconnect severed tissue during anastomosis procedures. The ability to avoid sutures provides significant advantages of avoiding the potential for damage to surrounding tissues and nerves that can be caused by installation of sutures using a needle. Such damage can include, for example in certain urethral anastomosis procedures, damage to ureters at the bladder or damage to the sphincter or nerves located in the perineal floor. Damage to any of these tissues has the potential to cause incontinence or impotence. Additionally, installing sutures is a difficult and technique-sensitive process that must typically be performed in a confined space and that would be avoided if possible based on other alternatives.

As additional advantage, inventive methods and devices, by eliminating sutures, can significantly reduce the amount of time required to perform certain anastomosis procedures. For example, the amount of time for suture installation during a vesico-urethral anastomosis can be in the range of from 20 to 30 minutes up to an hour. A suturing step of a retropubic procedure, for example, may take 20 or 30 minutes, or up to an hour for a laparoscopic procedure. These amounts of time may be significantly reduced, according to the invention, due to the elimination of a suturing step. Reduced procedure time also results in the attendant advantages of reduced patient time under anesthesia, which can reduce the cost and complication caused by anesthesia, as well as related general costs.

Embodiments of anastomosis devices of the invention include tissue approximating structure, such as one or multiple sets of tines. Tissue approximating structure may be remotely actuatable for approximation of severed tissues, by the use of an actuating mechanism that includes a knob or lever positioned at a convenient location on the device, such as at a proximal end of an anastomosis device.

According to the invention, anastomosis devices include an elongate body, tissue approximating structure, a drainage lumen, e.g., running as a channel within the elongate body, and mechanisms for actuating the tissue approximating structure, wherein the tissue approximating structure and related actuating mechanisms are isolated from the drainage lumen. According to certain configurations, tissue approximating structure and actuating mechanisms can also be isolated from the exterior of the anastomosis device. According to certain particularly preferred embodiments, tissue approximating structure and components of an actuating mechanism such as a wire are located internally to a wall of the anastomosis device, to prevent the components from being exposed to the drainage lumen or to elements external to the device.

In particular embodiments, the drainage lumen can be an open, unobstructed central channel along a length of the elongate body (e.g., an unobstructed drainage lumen), while tissue approximating structure and related mechanisms are located within a structure of the elongate body such as a body wall, e.g., isolated from the flow of bodily materials being drained (e.g., urine, blood, blood clots, or other bodily fluids or biological materials). A result is a minimum of exposure of the actuating mechanisms to bodily fluids.

Preventing contact between components of tissue approximating structure and related mechanisms, and bodily materials, can produce certain useful results. For instance, a bodily fluid such as urine can include salts and other materials that may become deposited on a mechanical actuating mechanism, causing the actuating mechanism to become "encrusted." An encrusted actuating mechanism may become difficult to operate, or inoperable. Preventing contact between the mechanism and the bodily fluid can reduce or prevent the possibility of materials becoming deposited on the mechanism, and the possibility of encrustation. Additionally, a tissue approximating structure or related mechanism, if located in a drainage lumen, can contact solid bodily materials that would flow through the drainage lumen, such as blood clots. A blood clot or other solid bodily material may become affixed to a tissue approximating structure or related mechanism, causing restricted flow or blockage of the drainage lumen. Positioning the tissue approximating structure and related mechanisms at a location other than within the drainage lumen, e.g., locating the tissue approximating structure and actuating mechanism in the wall of the anastomosis device, can reduce the potential for such blockage. Still additionally, an open drainage lumen may be used as a route for a guide wire, if necessary, to remove and replace an anastomosis device.

Methods of the invention can use an anastomosis device as described herein, including tissue approximating structure. Certain specific methods use anastomosis devices that also include features of a urethral catheter. Such devices can be used to cause healing during anastomosis, without sutures, and with draining of the bladder with a single anastomosis device. For example, an anastomosis device that includes features of a urethral catheter can be installed in a patient during or after a radical prostate removal procedure, and can remain installed with the bladder-draining function and the tissue-approximating function in effect until the anastomosis is completely healed and severed tissues, e.g., bladder and urethra, are re-connected by healing. Thus, an advantage associated with certain specific embodiments of inventive methods and devices can be that an anastomosis device performs dual functions when installed during and following an anastomosis procedure, of draining a bladder and functioning as a tissue approximating structure, at the same time.

According to the present description, the term "distal end" refers to a portion of an anastomosis device that is inserted into a body lumen during an anastomosis procedure such as tissue in the region of a bladder, urethra, urethral stump, or perineal wall. The term "proximal end" refers to a portion of an anastomosis device that is opposite from the distal end, including a portion that remains exterior to the body during use.

The terms "tissue approximating" and simply "approximating" refer to a process of bringing or holding body tissues in contact for healing. Examples include: the process of bringing severed surfaces of a bladder neck and a urethral stump, or two opposing severed urethral tissues, into contact for healing; and the process of holding severed surfaces of a bladder neck and a urethral stump, or two opposing severed urethral tissues, together for healing.

An aspect of the invention relates to an anastomosis device. The device includes: an elongate body comprising an open drainage lumen, a drainage aperture at a distal end of the device, in communication with a proximal end of the device through the drainage lumen, a balloon at the distal end, and tissue approximating structure extendable from the elongate body by use of an actuating mechanism.

Another aspect of the invention relates to an anastomosis device that includes: an elongate body having a bodywall, a proximal end, and a distal end; a drainage aperture at the distal end; a drainage lumen connecting the drainage aperture to the proximal end; an inflatable balloon at the distal end; an inflation lumen within a length of the body wall, connecting the balloon to the proximal end; distal tissue approximating structure comprising distal tines connected to a distal cylindrical frame, each distal tine extendably supported within an aperture of a tine deflector; a distal actuating mechanism operably connecting the distal to the proximal end of the device, through an actuating lumen in the body wall; proximal tissue approximating structure comprising proximal tines connected to a proximal cylindrical frame, each proximal tine extendably supported within an aperture of a tine deflector; and a proximal actuating mechanism operably connecting the proximal frame to the proximal end of the device, through an actuating lumen.

Another aspect of the invention relates to a method of performing urethral anastomosis. The method includes: inserting a portion of an anastomosis device into the urethra, the anastomosis device including: an elongate body comprising an open drainage lumen; a drainage aperture at a distal end of the device, in communication with a proximal end of the device through the open drainage lumen; a balloon at the distal end; and tissue approximating structure extendable from the elongate body by use of an actuating mechanism. The balloon is inflated in the bladder, and the tissue approximating structure is extended to hold severed tissue together.

Figure 1:
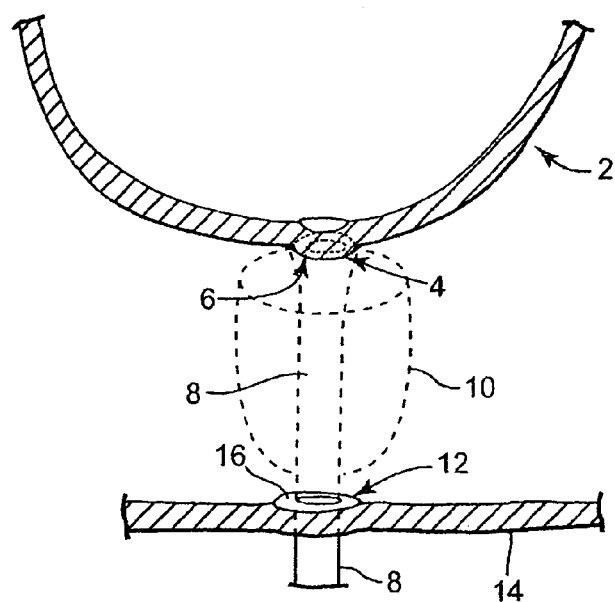
FIG. 1 is a partial cross-sectional view of internal body organs and illustrating general aspects of radical prostate removal.

All drawings are not necessarily drawn to scale.

DETAILED DESCRIPTION

An anastomosis device according to the invention can be any anastomosis device useful in the practice of an anastomosis procedure, e.g., as described herein, and including at least one tissue approximating structure and a related actuating mechanism isolated from a drainage lumen. An example of a useful design, generally, can include features of catheter devices sometimes referred to as Foley catheters, which generally include a thin, sterile tube with an attached balloon at its distal end. These catheters are typically inserted in the bladder to drain urine and are held in place by inflating the balloon. Such a standard Foley catheter may be modified to include the inventive features described herein, such as an elongate body having a drainage lumen, and tissue approximating structure and related actuating mechanisms located in isolation from the drainage lumen.

The various embodiments of the present invention each include an elongate body that may comprise a wide variety of configurations and components. For example, according to specific embodiments of the invention, an elongate body of an anastomosis device can be considered to be made up of multiple pieces of componentry that together provide an overall structure that allows the anastomosis device to function as described below. Specific pieces of the componentry may function, for example, by supporting or guiding a tissue approximating structure, or by assisting in performing other functions of an anastomosis device. Examples of such componentry include various parts such as spacers; sleeves; connective sheaths; lumen connectors; balloons; pieces useful to deflect or guide tissue approximating structure such as an extendable tine, during actuating (e.g., "tine deflectors"); adhesive materials to bond pieces or components together and form an air or water-tight seal; etc. Such componentry of a device, suitable structures and compositions of such componentry, and methods of producing such componentry and assembling such componentry into devices as described, will be appreciated by those of skill based on the present description and illustrations. Alternatively, the elongate body may include a single-piece construction having the desired functional features of a multiple-component elongate body. Such a one-piece elongate body may be molded, for example, to include the features desired for a particular elongate body.

An elongate body can include as at least a portion thereof, an elongate hollow shaft (e.g., a "catheter shaft") similar to catheter shafts used in devices such as a Foley catheter or other types of catheters, e.g., urinary catheters. In some configurations, the elongate body will comprise only a catheter shaft or hollow shaft (in which case, the elongate body and the catheter shaft will be the same component of the structure), while in other configurations, the catheter shaft or hollow shaft portion will be one of multiple pieces of an elongate body construction. In either case, at least a portion of the elongate body can generally be of a flexible polymeric, biocompatible material such as a cured, extruded silicone material. The elongate body can be sufficiently flexible to be useful as a urethral catheter, and may be of a single or multi-piece construction. Lumens are included in the elongate body, including, e.g., a drainage lumen, and an actuating lumen for tissue approximating structure. A drainage lumen may typically be a lumen extending along the substantial length of the elongate body, often within a central portion of the elongate body, e.g., a "central lumen" or "central drainage lumen" that includes the central lengthwise axis of a hollow elongate, flexible catheter shaft portion or elongate body. The elongate body can also include one or more additional lumens to operate with other features of a device, e.g., an inflation lumen for a distal end balloon.

The elongate body of an anastomosis device of the present invention, or pieces thereof such as a catheter shaft, can include a body wall of a thickness that provides for desired properties of an anastomosis device, e.g., a thickness that allows for: useful mechanical properties of strength, flexibility, etc.; placement of a drainage lumen within a central channel; placement of tissue approximating structures and related mechanisms; and optional placement of other lumens within or against a wall of an elongate body. Exemplary embodiments of a wall of an elongate body or a wall of a portion of an elongate body, can be defined as a solid wall of a hollow cylindrical body, such as the body of a catheter shaft portion of a device, wherein the body wall defines an outer surface and a hollow inner space or central lumen, which normally functions as the drainage lumen.

Other portions of an elongate body of the present invention, e.g., at portions of a device proximal to tissue approximating structure, can include a body wall that is composed of multiple pieces or componentry as described herein. For example, an elongate body may include multiple length-wise or circumferential-wise sections or pieces, which when connected together can operate to maintain or support tissue approximating structure and other features of an anastomosis device. Examples of elongate bodies include multiple elongate sections or portions, e.g., fully or partially concentric or cylindrical layers, multiple materials, length-wise pieces or sections, a catheter shaft, lumen connectors, connective sheaths, coatings, spacers, etc., and other components that combine to produce a useful design. In other words, an elongate body as described herein may be constructed of multiple pieces, layers, extensions, or elements that can be assembled together in a length-wise, concentric, or other manner, to form a multi-piece elongate body of an anastomosis device, wherein the anastomosis device includes the elongate body, and wherein the elongate body defines a drainage lumen and includes tissue approximating structure and an actuating lumen.

According to the invention, the elongate body, including componentry, defines a drainage lumen, at least a length of which does not contain tissue approximating structure or a component thereof, such as an actuating mechanism. Such a device can include what is referred to as an "open" or "unobstructed" drainage lumen. According to such embodiments, a drainage lumen, e.g., a central channel running substantially the length of an anastomosis device (from a proximal end to drainage apertures at a distal end of the device), can be open along such a length and not contain a component of a tissue approximating structure, an actuating mechanism, or any other component of the anastomosis device that would inhibit the flow of a fluid or other bodily material through the drainage lumen.

The open drainage lumen can be defined by one or multiple pieces of the elongate body. In specific embodiments, an inside wall surface of a catheter shaft can define at least a portion of a total length of a drainage lumen. Other portions of the length of a drainage lumen can be defined by other pieces or componentry of an elongate body, such as a drainage lumen connector, as described elsewhere herein. Thus, of the entire length of an open drainage lumen, from a proximal end of a device to drainage apertures, the cross-section of the drainage lumen may be of a uniform or non-uniform cross section or shape, e.g., circular or non-circular, along different portions of the length of the device, while still being "open" and not containing tissue approximating structure or any related mechanisms. A drainage lumen can be considered to be "open" or unobstructed even if a portion of the open drainage lumen has a non-circular or irregular cross-section, or if the lumen does not include a uniform diameter along the entire length of the lumen.

Figure 10A:
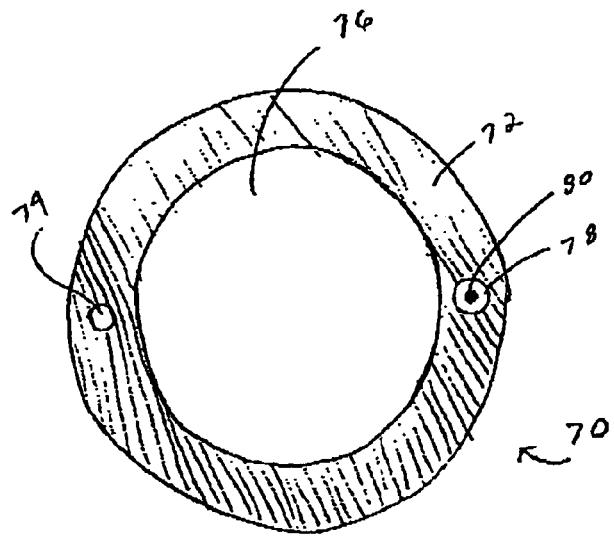
FIGS. 10a, 10b, and 10c are cross-sectional end views of three embodiments of elongate body portions of anastomosis devices of the invention, each including an open drainage lumen or channel.
Figure 10B:
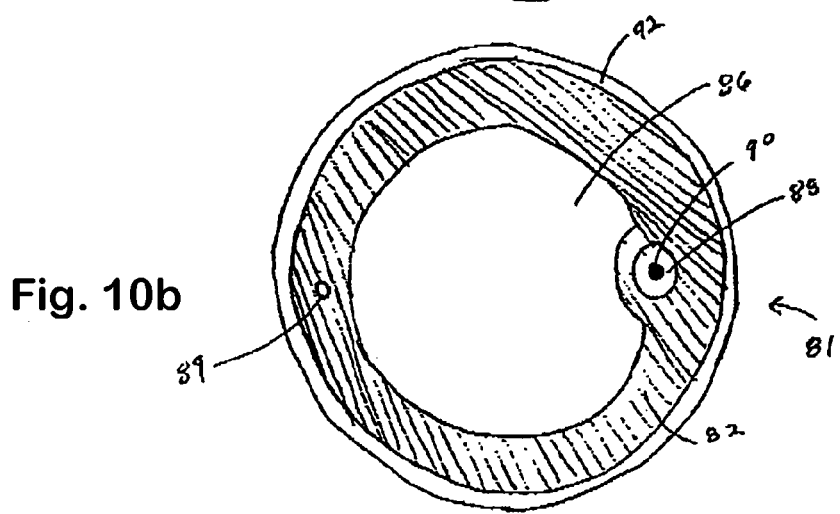
Figure 10C:
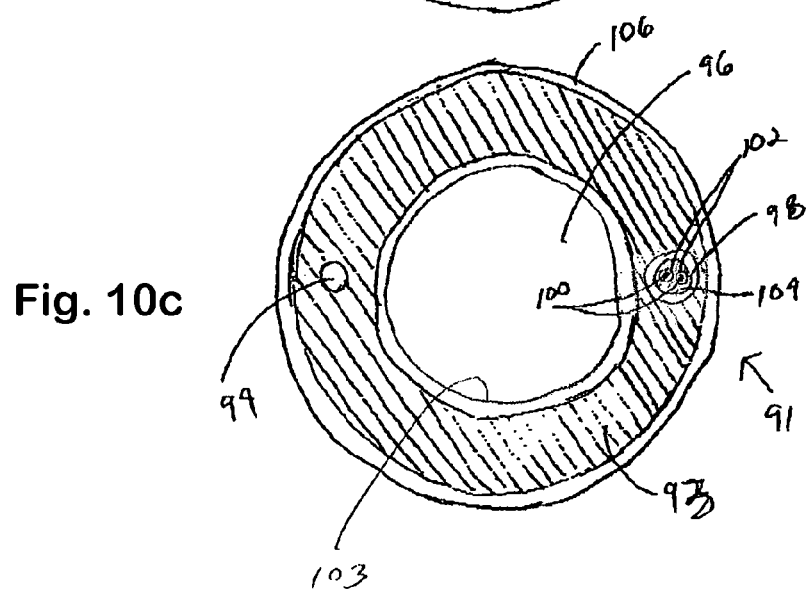

For purposes of illustration, FIGS. 10a, 10b, and 10c are included to show certain specific features of exemplary constructions of elongate bodies of devices of the invention, in cross section, and having open drainage lumens in the form of a central channel. A wide variety of other cross-sectional shapes are contemplated by the invention, however, as discussed above.

Referring to FIG. 10a, elongate body 70 includes body wall 72, an interior surface of which defines an open drainage lumen 76. Inflation lumen 74 is an aperture extending lengthwise through at least a portion of the length of body wall 72, and actuating lumen 78 also extends through at least a portion of the length of body wall 72. Actuating mechanism 80, e.g., in the form of a wire or shaft, extends from a proximal end of the device to tissue approximating structure within lumen 78.

Referring to FIG. 10b, which illustrates another example of a cross section of an elongate body, elongate body 81 includes body wall 82, which defines an open central drainage lumen 86, inflation lumen 84 extending through at least a portion of the length of body wall 82, and actuating lumen 88 also extending through at least a portion of the length of body wall 82. Actuating mechanism 90, e.g., in the form of a wire or shaft, extends from a proximal end of the device to tissue approximating structure, within lumen 88. Elongate body 81 of FIG. 10b also includes outer sheath 92. As shown, the portion of wall 82 adjacent to the actuating lumen 88 protrudes partially into the generally circular area of the drainage lumen 86, thereby making the cross-sectional shape of the elongate body irregular. However, the drainage lumen 86 is still considered to be an open drainage lumen in this area.

Referring to FIG. 10c, which illustrates another example of an elongate body of the invention, elongate body 91 includes body wall 93, which defines an open central drainage lumen 96, inflation lumen 94 extending through at least a portion of the length of the body wall 93, and actuating lumen 98 also extending through at least a portion of the length of body wall 93. Dual actuating mechanisms 100, e.g., in the form of two wires or shafts extending from a proximal end of the device to tissue approximating structures, are shown to be present in lumen 98. Actuating mechanisms 100 are further contained in a bitumen housing 104, which contains two lumens 102, each of which includes one of the actuating mechanisms 100. Elongate body 91 of FIG. 10c also includes outer sheath 106 and lumen connector 103. Not shown, but preferably present in a bitumen housing 104, is a reinforcement that prevents the housing from stretching, and thereby provides a constant distance between proximal and distal ends of housing 104, to allow precise control of the tissue approximating structures when activated using activating mechanism 100. The reinforcement can also facilitate assembly of an anastomosis device, e.g., by providing sufficient strength for a housing 104 to be pulled through an aperture in a wall of an elongate body. Reinforcement or outer sheaths may be optionally utilized with any of the various embodiments of the present invention.

Tissue approximating structure according to the invention can be the structure or component of an anastomosis device of the invention that can be used to cause or maintain contact between severed tissues for anastomosis, such as severed urethral tissues, or such as severed tissue of the bladder or bladder neck with severed tissues of a urethral stump or perineal floor, to hold severed tissue surfaces in contact for healing. Thus, tissue approximating structure can be located at a position of an anastomosis device to allow contact with tissue for approximation. The tissue approximating structure may include, for example, one or multiple balloon or balloon-like structures that can be placed against tissues for anastomosis. Alternately, tissue approximating structure may include elongate structure such as a needle, tine, prod, probe, or the like, which may have a blunt or a sharp end and may be extendable from an elongate body of an anastomosis device at a location where the tissue approximating structure can approximate tissue for healing, e.g., at the distal end of the device where the structure will be near desired tissue, for example the bladder or perineal wall (when installed), or at a severed urethra below the perineal floor (when installed).

A specific example of a useful type of tissue approximating structure can be in the form of a sharp or blunt elongate structure (e.g., a sharp-ended needle or tine) that can be extended from the elongate body to contact and optionally penetrate into or through tissue for approximation, e.g., tissue selected from one or more of a tissue of the bladder, bladder neck, urethra, bulbar urethra, urethral stump, or perineal floor, to place opposing severed tissue surface into contact for healing, and preferably also to hold the tissues in contact with each other during the healing period. Combinations of balloons and extendable elongate structures may also be useful in certain applications. Tissue approximating structure does not require and can preferably exclude sutures and any component or structure designed to function in combination with a suture or suturing device such as a needle used to install a suture. Tissue approximating structure can include support structure such as a frame for supporting elongate elements (e.g., tines) as well as an actuating mechanism.

Tissue approximating structure can be extendable, e.g., from a retracted or withdrawn position inside of or along the elongate body (e.g., for tines or needles) or a non-inflated position (for a balloon), to an employed or extended or otherwise "non-retracted" position. In the extended position, wherein the tissue approximating structure extends beyond the dimension (diameter) of the elongate body, e.g., as with a tine that extends through a body wall or as with a balloon that is inflated beyond the outer walls of the elongate body, the tissue approximating structure can be positioned to contact a tissue and facilitate healing between severed tissues.

A tissue approximating structure can be actuated (e.g., extended or retracted) by any useful method, device, or structure, for example as illustrated in the attached figures, such as by an actuating mechanism connecting the tissue approximating structure to a proximal end of an anastomosis device. The actuating mechanism may be in the form of a narrow, elongate wire or shaft that is sufficiently rigid and flexible to actuate tissue approximating structure as described. The wire or shaft may be made, e.g., from a metal, metal alloy, a polymeric material such as a plastic, or similar material. Materials used for an actuating mechanism may be of the same material as the tissue approximating structure, or may be a different material secured to the tissue approximating structure.

According to the invention, one or more of tissue approximating structure and related components of an actuating mechanism are preferably located within the device to not interfere with the flow of a bodily material through the open drainage lumen of the device. For example, components of tissue approximating structure and actuating mechanisms may be located at positions other than with the drainage lumen, e.g., within components of a wall of an elongate body.

As a specific example, a lumen that contains an actuating mechanism in the form of a wire, shaft, or other similar type of actuating mechanism, may be contained in a solid wall of an elongate body such as a portion of an elongate body defined by a catheter shaft. See, e.g., the actuating lumens 78, 88, and 98 of FIGS. 10a, 10b, and 10c, respectively. Alternatively or in addition, a lumen of an actuating mechanism may also extend into, through, or past other componentry of an elongate body such as componentry to support a tissue approximating structure, e.g., a spacer, tine deflector, connector, etc.

Particular examples of tissue approximating structures can also be designed to be placed in a wall of an elongate body. As a specific example, tissue approximating structure of the elongate form, e.g., tines, can be constructed as at least one elongate structure attached to a ring-shaped, circular, or cylindrical support or frame. The frame may support multiple elongate structures at a circumference that allows the elongate structures to extend from a central portion of an elongate body of a device, e.g., isolated from a drainage lumen positioned centrally to an elongate body. The frame may be of the same material or a different material as the elongate structures of the tissue approximating structure, and the elongate structures may be held to the frame by any useful mode, e.g., adhesive or welding. Optionally, a frame and elongate structures may also be of a single-piece construction, also optionally including the actuating mechanism.

Figure 5A:
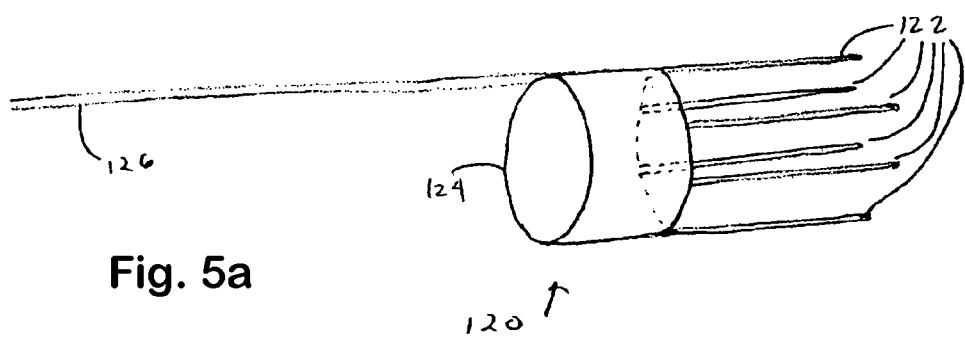
FIGS. 5a and 5b are perspective views of two embodiments of tissue approximating structure according to the invention.
Figure 5B:
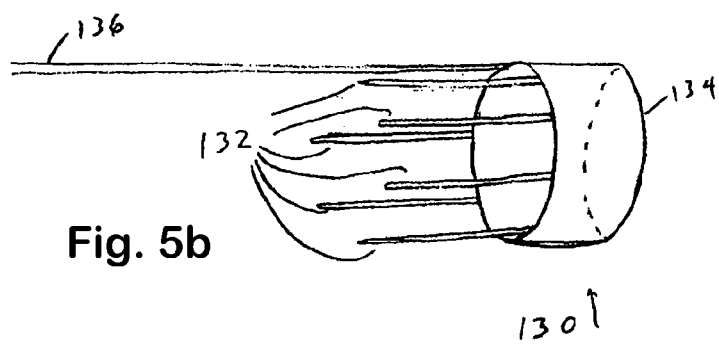

FIGS. 5a and 5b illustrate exemplary elongate tissue approximating structure (e.g., tines) attached to a circular (e.g., cylindrical) frame, with the frame also being attached to an actuating mechanism. Preferably, the shape of the frame generally corresponds to the shape of the elongate body in the area of the elongate body in which it will be positioned. Further, the frame preferably includes an internal opening or passageway that generally corresponds to the shape of the open central lumen of the elongate body in which the frame will be positioned. Referring to FIGS. 5a and 5b, these show exemplary tissue approximating structures 120 and 130, respectively. Each structure 120 and 130 includes a set of six tines (122 and 132), each attached to a support ring or frame 124 and 134, respectively. Each structure 120 and 130 also includes an actuating mechanism 126 and 136, respectively. The actuating mechanisms 126, 136 both extend toward a proximal end of an anastomosis device when positioned therein. As such, structure 120 can be included within an elongate body as a proximal tissue approximating structure, in that tines 122 extend away from actuating mechanism 126 so that, when installed, tines 122 can be extended from an elongate body by movement of actuating mechanism 126 toward a distal end of an anastomosis device. Tissue approximating structure 130 can be included within an elongate body as a distal tissue approximating structure, in that tines 132 extend toward actuating mechanism 136 so that tines 132, when installed in an anastomosis device, can be actuated by movement of actuating mechanism 136 toward a proximal end of an anastomosis device.

Tissue approximating structure in the form of elongate tines and a supporting ring or frame can be used in combination with a support (e.g., a "tine support" or "tine deflector") that supports and directs the tines during use. A tine support or tine deflector can be any device or component included in an assembled anastomosis device that directs or deflects an elongate tissue approximating structure during actuation (e.g., extension and retraction). Such a component can be in the form of a part or piece of an anastomosis device (e.g., componentry) that contacts, guides, or otherwise supports elongate tissue approximating structure and that during actuation causes the elongate tissue approximating structure to deflect in a desired direction in extension from the elongate body. Alternatively, a tine deflector may be incorporated within the structure of another component or piece of an anastomosis device so that the tine deflector is integral to the structure of the other component. For example, a tine deflector may not be a separate piece or component, but may instead be a series of openings or apertures through a wall of a portion of an elongate body for directing the tines in a particular direction. In any case, it is preferable that the interior surfaces of the apertures through which the tines are directed are made of a low-friction material to allow for relatively easy movement of the tines through the openings. It is further preferred that any such apertures are smooth and that they curve or direct the tines along a relatively smooth path so that the process of deflecting the tines is relatively easy. A tine deflector or similar component or structure of an anastomosis device can be located at a position along the length of an anastomosis device that is proximal the elongate tissue approximating structure affected by the tine deflector. As such, a tine deflector may be located at a position along a length of an anastomosis device such that when the device is installed in a patient, the tine deflector will be proximal to tissue for approximation.

Figure 6:
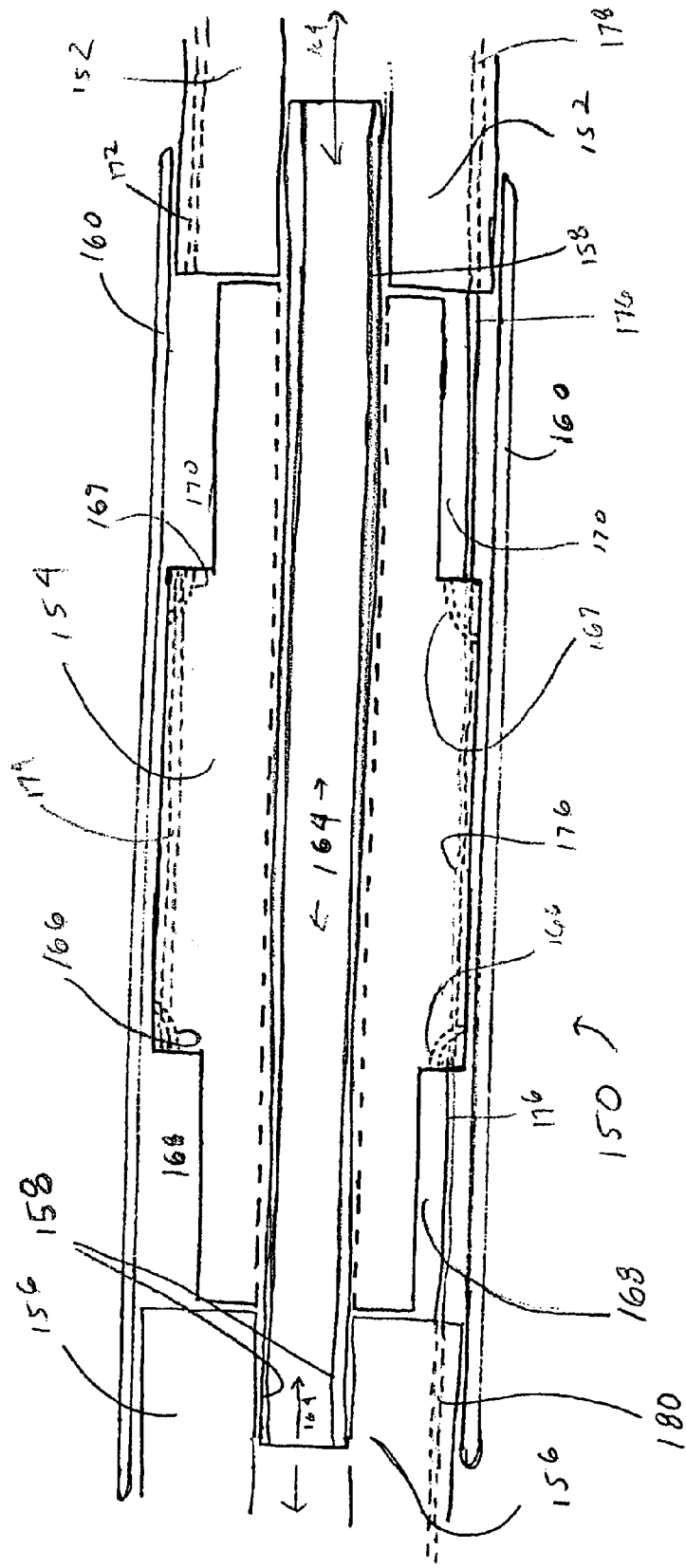
FIG. 6 is a cross-sectional view of one embodiment of an elongate body of devices of the invention.
Figure 7:
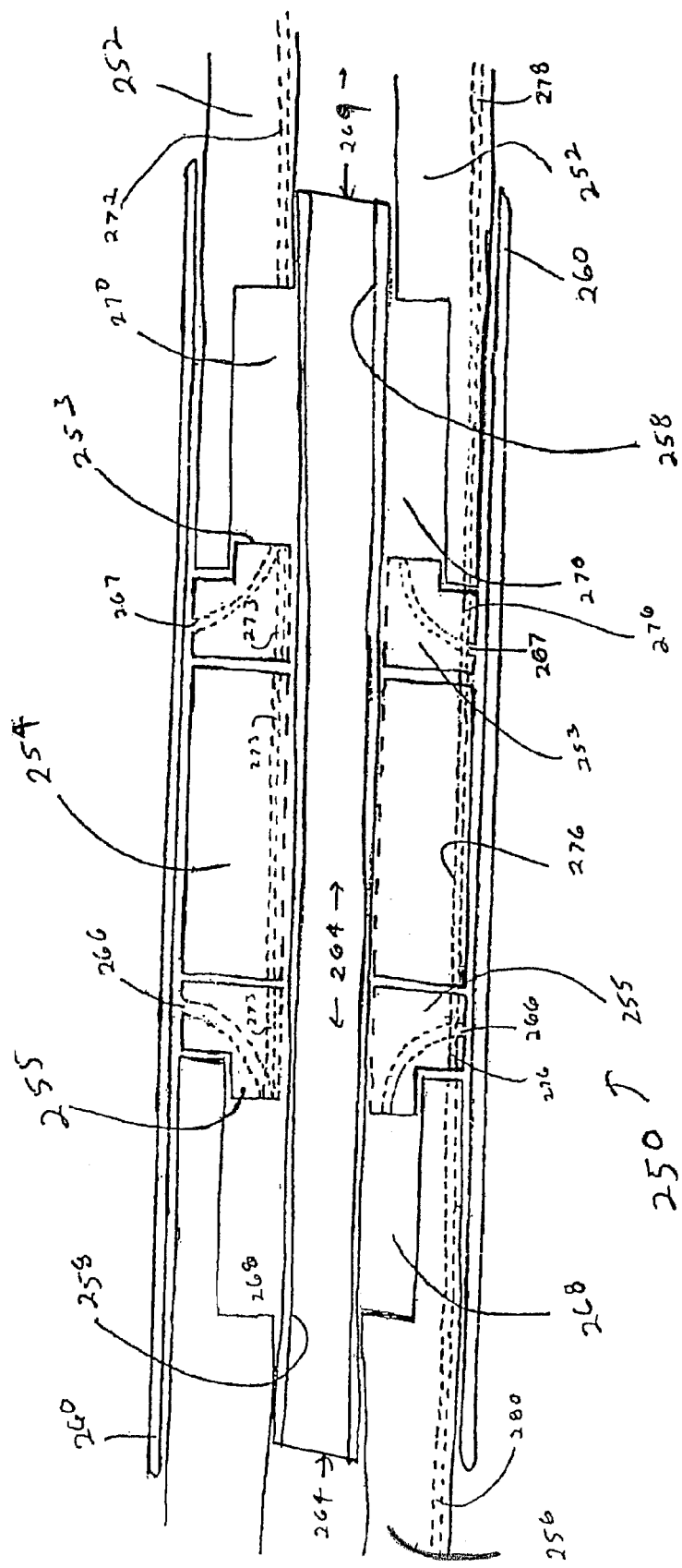
FIG. 7 is a cross-sectional view of another embodiment of an elongate body of the present invention.

FIGS. 6 and 7 are cross-section illustrations of embodiments of portions of elongate bodies of anastomosis devices of the invention, including componentry designed and assembled to result in an anastomosis device that supports and directs tissue approximating structure, while including an open drainage lumen. These constructions and components are considered to be exemplary structures, where the scope of the invention is intended to include devices having more or less components than those described below (e.g., multiple described components could instead be included within a single component having multiple functions). Further, the various components may be attached or positioned relative to each other by any number of securing methods as are well known in the art. As described herein, the left side of the device in the illustration is considered to be the distal direction and the right side of the device is considered to be the proximal direction.

Referring to FIG. 6, there is illustrated a portion of an elongate body 150 of a tissue approximating device that includes a distal end of a catheter shaft 152, tine deflector 154, proximal end of a distal tip 156, drainage lumen connector 158, and connective sheath 160. Each of catheter shaft 152, tine deflector 154, connective sheath 160, and drainage lumen connector 158 can be generally cylindrical and hollow, to define an assembled body wall of elongate body 150 that includes open drainage lumen 164.

The separate pieces or componentry of the assembled body 150 can be made of materials useful in surgical devices such as catheters, that can be formed into the specific structures of the various componentry, and that can then be assembled into an anastomosis device as described. For example, each piece can be prepared from a desirably flexible or rigid material that can typically be a polymeric material and that may be formed by one or more methods of extrusion, injection molding, or similar useful methods. For example, catheter shaft 152 may be made of an extruded cured silicone polymer or a similarly flexible material.

Tine deflector 154 may be made of a material that allows for elongate tissue approximating structure to slide easily through apertures 166 and 167, e.g., a relatively rigid polymeric material such as a rigid plastic, e.g., a polycarbonate.

Connective sheath 160 may be made of a material that is also relatively flexible and which, during assembly, is capable of being placed (e.g., slid) over and optionally adhered or otherwise attached to some portion or portions of an assembly of the distal tip 156, tine deflector 154, and catheter shaft 152, as illustrated. Additionally, connective sheath 160 can be capable of having one or more elongate tissue approximating structures pierce through the connective sheath when part of the assembled device. The connective sheath can be useful to keep external fluids from contacting the tissue approximating structure or related mechanisms, and can also provide an anastomosis device with a relatively smooth external profile.

Drainage lumen connector 158 can generally be a hollow tubing, such as a polymeric straw or hollow core. Connector 158 can be prepared of any desired material, such as a desirably rigid or flexible polycarbonate, silicone, etc. Similarly, distal tip 156 may also be prepared of any desired material, such as a desirably rigid or flexible polycarbonate, silicone, etc.

In FIG. 6, distal end of catheter shaft 152 abuts proximal end of tine deflector 154, and distal end of tine deflector 154 abuts a proximal end of distal tip 156, to provide a portion of elongate body 150, with drainage lumen connector 158 internally engaging and connecting distal tip 156 to catheter shaft 152 while extending internally through tine deflector 154. A continuous open drainage channel 164 extends through drainage lumen connector 158, from catheter shaft 152, through tine deflector 154, to distal tip 156, and to drainage apertures (not shown) in distal tip 156. Connective sheath 160 also engages and connects catheter shaft 152, tine deflector 154, and distal tip 156, externally, also providing a continuous elongate body 150. The separate pieces of the assembled componentry can also be connected together by an adhesive to provide an air and watertight seal, e.g., a silicone adhesive.

Still referring to FIG. 6, the portion of elongate body 150 can include tissue approximating structure, as described herein, but which is not shown. Tissue approximating structure can be located in a position within the elongate body 150 that is isolated from and that does not expose the tissue approximating structure or related mechanisms to the interior of drainage lumen 164, e.g., in circumferential spaces 168 and 170, which are illustrated as open cylindrical spaces defined by and between the distal and proximal ends, respectively, of tine deflector 154, and internal surfaces of connective sheath 160. Tine support 154 is generally cylindrical having reduced-diameter proximal and distal ends, each of which can slidably support a cylindrical or ringed tine frame having attached elongate tissue approximating structure (e.g., as shown in FIGS. 5*a* and 5*b*). Tine support 154 also includes arcuate distal and proximal apertures 166 and 167 (dashed lines), through which elongate tissue approximating structures (not shown) can be supported and guided (e.g., deflected) when actuated.

Referring still to FIG. 6, a cylindrical or ring-shaped proximal tine frame can be included within space 170. The tine frame can be connected to at least one (e.g., 1, 2, 4, or 6, etc.) elongate tissue approximating structures ("tines"), each of which can extend through a proximal aperture 167 of tine deflector 154. The tine frame (not shown) can be connected to a proximal tissue approximating structure actuating mechanism (also not shown) (e.g., a wire, shaft, or the like) at a location of the ring or cylinder circumference. The proximal actuating mechanism can extend through an aperture 172 (dashed lines) within a wall of catheter shaft 152. The proximal actuating mechanism can be extended and retracted, distally and proximally, to actuate tines of the proximal tissue approximating structure, whereby the tines will be guided and deflected through proximal apertures 167 to be extended (or retracted) through connective sheath 160, to contact tissue for approximation.

Similarly, a cylindrical or ringed distal tine frame can be included within distal space 168. The tine frame can be connected to at least one (e.g., 1, 2, 4, or 6, etc.) elongate tissue approximating structures ("tines"), each of which extends through a distal aperture 166. The tine frame (not shown) can be connected to a distal tissue approximating structure actuating mechanism (also not shown) (e.g., a wire, shaft, or the like) at a location of the ring or cylinder circumference. The distal actuating mechanism can extend through an aperture, slot, or the like 174, within tine deflector 154, and then through aperture 172 (dashed lines) within catheter shaft 152. The distal actuating mechanism can be extended and retracted, distally and proximally, to actuate tines of the distal tissue approximating structure, whereby the tines will be guided and deflected through distal apertures 166 to be extended (or retracted) through connective sheath 160, to contact tissue for approximation.

Also shown in FIG. 6 is a portion of a continuous inflation lumen 178 that connects a balloon (not shown) located at a distal end of the anastomosis device, to a proximal end, to allow inflation of the balloon. Inflation lumen 178 is preferably included within a solid wall of catheter shaft 152, and communicates with a proximal end of the anastomosis device. Inflation lumen 180 is included in a solid body wall of distal tip 156, and communicates with a balloon. Inflation lumen connector 176 is preferably a solid tube, straw, or otherwise useful fluid-tight connector that extends through a space, aperture, slot, or other opening (not shown) within or past tine deflector 154, while connecting inflation lumens 178 and 180. Inflation lumen connector 176 can be made of a useful fluid-tight polymeric or metal material that is capable of being assembled as illustrated. As one example, an inflation lumen connector 176 can be a tube of the metal alloy Nitinol. The result is a continuous inflation lumen extending along the length of the illustrated portion of elongate body 150, from catheter shaft 152 (including inflation lumen 178), through inflation lumen connector 176, to distal tip 156 (including inflation lumen 180), and then in communication with a balloon of the anastomosis device. Optionally and preferably, an adhesive is used to connect inflation lumen connector 176 to catheter shaft 152 and to distal tip 156 to produce a fluid-tight bond; however, other connection techniques can be used. It is further contemplated that the inflation lumen comprising lumens 176, 178, and 180 instead comprise more or less lumen pieces.

Referring now to FIG. 7, there is illustrated a portion of another embodiment of an elongate body 250 of a tissue approximating device that includes an end 252 that could be, e.g., a distal end of a catheter shaft or another housing or spacer; proximal tine deflector 253; spacer 254, distal tine deflector 255; end 256, e.g., of distal a tip; drainage lumen connector 258; and connective sheath 260. Each of end 252, tine deflectors 253 and 255, connective sheath 260, and drainage lumen connector 258, can be generally cylindrical and hollow, to define a body wall of elongate body 250 that includes open drainage lumen 264.

The separate pieces or componentry of the assembly of elongate body 250 can be made of materials useful in surgical devices such as catheters, and that can be prepared and assembled to produce an anastomosis device as described. The different pieces of the assembled componentry, such as a catheter shaft or other housing or spacer (252), distal and proximal tine deflectors, drainage lumen connector, connective sheath, distal tip, and inflation lumen connector, can be of materials as described in the embodiment of FIG. 6. Spacer 254, as illustrated, can be a suitably rigid or flexible material capable of maintaining the position of adjacent components relative to each other, such as a rubber, polymeric carbonate, silicone, etc., or a rigid or flexible foam material. Certain preferred devices of the invention can include a spacer material that is relatively flexible, such as a flexible cured silicone or a similar flexible material. A relatively flexible material can result in a relatively more flexible portion 250 of an anastomosis device, compared to a similar device having a spacer prepared from a relatively more rigid material.

In FIG. 7, end 252 abuts a proximal end of proximal tine deflector 253; distal end of proximal tine deflector 253 abuts a proximal end of a spacer 254; distal end of spacer 254 abuts a proximal end of distal tine deflector 255; and distal end of distal tine deflector 255 abuts a proximal end of end 256. The assembly of these components provides a continuous portion of elongate body 250, with drainage lumen connector 258 internally engaging and connecting end 256 to end 252 while extending internally through tine deflectors 253 and 255, and spacer 254. A continuous open drainage lumen 264 extends through lumen connector 258 from end 252, through proximal tine deflector 253, through spacer 254, through distal tine deflector 255, to end 256 and to drainage apertures (not shown) in end 256. Connective sheath 260 also engages and connects end 252, proximal tine deflector 253, spacer 254, distal tine deflector 255, and end 256, externally, also providing a continuous elongate body 250. The separate pieces of the assembled componentry can also be connected together by an adhesive such as a silicone adhesive, to provide an air and fluid (e.g., water)-tight seal.

Still referring to FIG. 7, the portion of elongate body 250 can include tissue approximating structure, as described herein, but which is not shown. Tissue approximating structure can be located in a position within the elongate body 250 that is isolated from and that does not expose the tissue approximating structure or related mechanisms to the interior of drainage lumen 264, e.g., in circumferential spaces 268 and 270. Space 268 is an open cylindrical space defined by and between surfaces of distal tine deflector 255, end 256, and connector 258. Space 270 is an open cylindrical space defined by and between surfaces of proximal tine deflector 253, end 252, and drainage lumen connector 258. Distal tine deflector 255 and proximal tine deflector 253 are generally cylindrical, having reduced-diameter distal and proximal ends, respectively, each of which can slidably engage elongate tines supported by a cylindrical or ringed tine frame that is slidably supported by drainage lumen connector 258. Distal and proximal tine supports 255 and 253 also include distal and proximal apertures 266 and 267, respectively, through which elongate tissue approximating structures (not shown) can be extended.

Still referring to FIG. 7, a cylindrical or ringed proximal tine frame (not shown) can be included within space 270. The proximal tine frame can be connected to multiple (e.g., 2, 4, or 6, etc.) proximal elongate tissue approximating structures ("tines"), each of which can extend through a proximal aperture 267. The proximal tine frame (not shown) can be connected to a proximal tissue approximating structure actuating mechanism (also not shown) (e.g., a wire, shaft, or the like) at a location of the ring or cylinder circumference. The proximal actuating mechanism can extend through an aperture 272 (dashed lines) within a wall of end 252 and a connected elongate body. The proximal actuating mechanism can be extended and retracted, distally and proximally, to actuate tines of the proximal tissue approximating structure, whereby the tines will be guided and deflected through proximal apertures 267 to be extended (or retracted) through connective sheath 260, to contact tissue for approximation.

Similarly, a cylindrical or ringed distal tine frame can be included within space 268. The distal tine frame can be connected to multiple (e.g., 2, 4, or 6, etc.) distal elongate tissue approximating structures ("tines"), each of which extends through a distal aperture 266. The distal tine frame (not shown) can be connected to a distal tissue approximating structure actuating mechanism (also not shown) (e.g., a wire, shaft, or the like) at a location of the ring or cylinder circumference. The distal actuating mechanism can extend through aligned apertures, slots, or the like (dashed lines 273) that extend through distal tine deflector 255, spacer 254, proximal tine deflector 253, and then through aperture 272 (dashed lines) within end 252. The distal actuating mechanism can be extended and retracted, distally and proximally, to actuate tines of the distal tissue approximating structure, whereby the tines will be guided and deflected through distal apertures 266 to be extended (or retracted) through connective sheath 260, to contact tissue for approximation.

Also shown in FIG. 7 is a portion of a continuous inflation lumen that connects a balloon (not shown) located at a distal end of the anastomosis device to a proximal end, to allow inflation of the balloon. Inflation lumen 278 is included in end 252, and communicates with a proximal end of the device. Inflation lumen 280 is included in end 256, and communicates with a balloon at the distal end. An inflation lumen connector (not shown), which can be a solid, tube, straw, or similar air-tight structure, can extend through aligned apertures, slots, or other openings (dashed line 278, 276, 280, and the like) within end 252, distal and proximal tine deflectors 255 and 253 spacer 254, and end 256, to connect inflation lumens 278 and 280. As one example, an inflation lumen connector may be a tube of the metal alloy Nitinol. The result is a continuous inflation lumen extending along the length of the illustrated portion of elongate body 250, from end 252 to end 256. Optionally and preferably, an adhesive can be used to connect inflation lumen connector 276 to end 252 and to end 256, to produce a fluid-tight bond.

Figure 8:
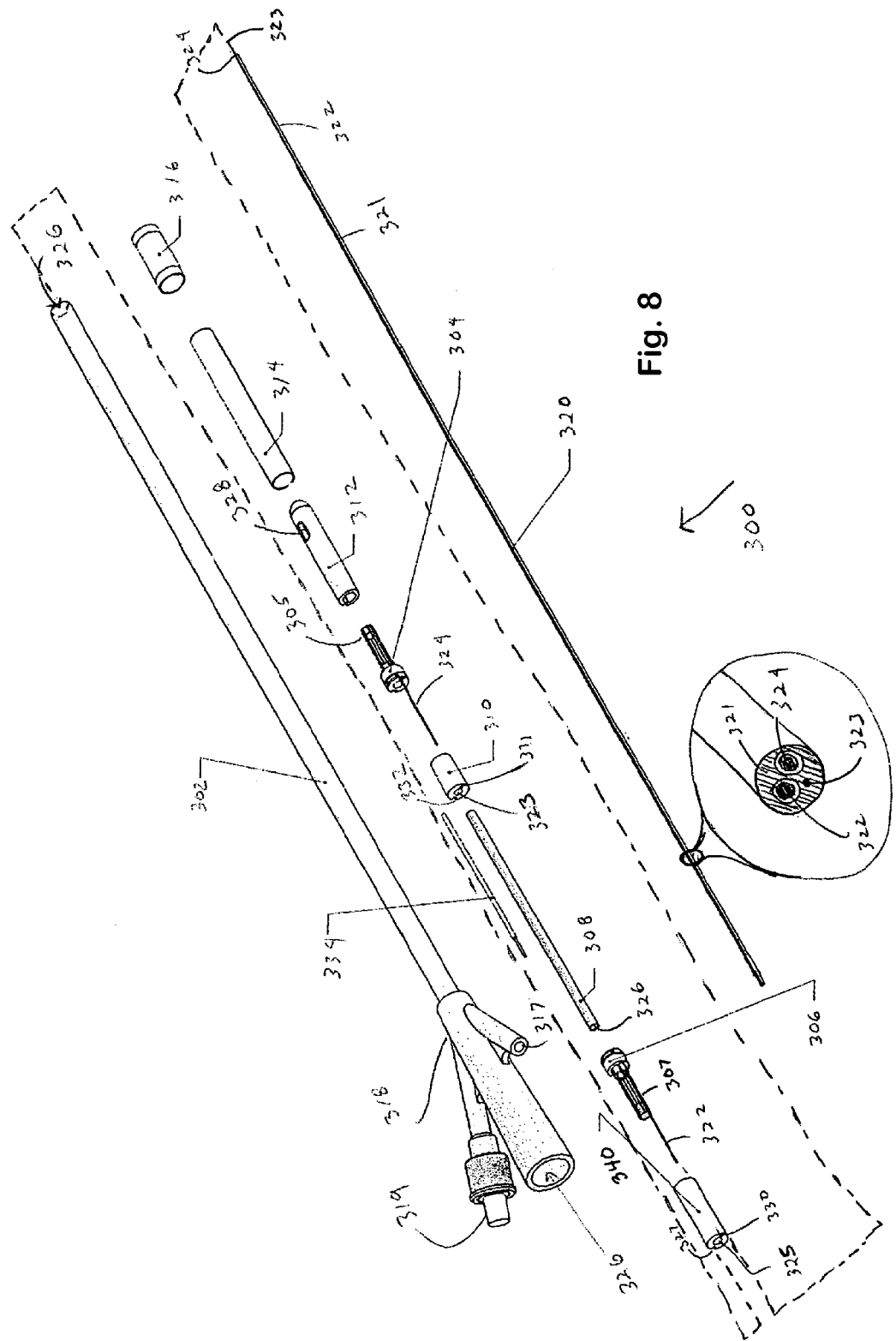
FIG. 8 is an exploded perspective view of multiple components that comprise one preferred embodiment of an anastomosis device of the invention.

Another embodiment of an anastomosis device according to the invention is illustrated at FIG. 8. FIG. 8 is an exploded view of an anastomosis device 300, to illustrate assembly of components of an anastomosis device. The dashed lines are intended to illustrate the general orientation of the various components relative to each other when assembled, where like numerals refer to like components. Catheter shaft 302 includes an open central drainage lumen 326 in the form of a hollow interior channel defined by an inner surface of a substantially solid wall of the catheter shaft 302. Catheter shaft 302 additionally includes an inflation lumen (not shown) and an actuating lumen (not shown), each of the inflation lumen and actuating lumen being in the form of a lengthwise aperture extending along the length of the catheter shaft within the otherwise solid wall of the catheter shaft 302. Catheter shaft 302 is attached at a proximal end to funnel 318, which includes a port in communication with drainage lumen 326, as well as port 319 in communication with the inflation lumen (not shown) of catheter shaft 302, and port 317 in communication with actuating lumen (not shown) of catheter shaft 302.

When assembled, the distal end of catheter shaft 302 abuts housing 340, which includes an actuating lumen 330, central opening 325 sized to fit over drainage lumen connector 308, and slot or aperture 327 sized and positioned to allow inflation lumen extender 334 to pass through or next to housing 340.

Actuating mechanism assembly 320 includes a bitumen tubing 321 (shown at insert in close-up cross section). Bi-lumen tubing 321 includes two lumens, one each for proximal actuating mechanism 322 and distal actuating mechanism 324, and also includes an optional reinforcement structure 323, which can be a flexible metal wire running internally along the length of bitumen tubing 321. Bi-lumen tubing 321 can be prepared from any material that allows use as a bitumen tubing, e.g., a low friction polymeric material that can be reinforced to sufficient strength, while remaining flexible, to allow actuation of distal and proximal actuating mechanisms without stretching, by pushing or pulling of an actuating mechanism contained in the tubing 321. Actuating mechanism assembly 320 can be inserted into the actuating mechanism lumen (not shown) of catheter shaft 302 (e.g., by pulling on the reinforced bitumen tubing or reinforcing wire 323) to position each actuating mechanism 322, 324 to extend from port 317 at the proximal end of the device 300, to each of the proximal and distal tissue approximating structures 307 and 305.

Proximal tissue approximating structure 307 is connected to proximal actuating mechanism 322. Proximal tissue approximating structure 307 includes multiple elongate tissue approximating structures (e.g., tines) attached to a cylindrical frame, the frame connecting to proximal actuating mechanism 322, which mechanism is preferably long enough to allow for a desired manipulation by the user for actuation of the structure 307. The proximal frame and tines are supported by drainage lumen connector 308 and proximal tine deflector 306. Spacer 310 is located between proximal tine deflector 306 and distal tine deflector 304, and includes a central aperture 342 sized to fit over drainage lumen connector 308; space, slot, or aperture 332 sized to fit over inflation lumen extender 334; and actuating lumen 331 sized to fit over bitumen tubing 321. Distal tine deflector 304 is supported by drainage lumen connector 308 and deflects distal tissue approximating structure 305, which includes elongate tissue approximating structure (tines) attached to a cylindrical or ring-shaped frame, the frame connecting to distal actuating mechanism 324, which mechanism is preferably long enough to allow for a desired manipulation by the user for actuation of the structure 305. Each of proximal tine deflector 306 and distal tine deflector 304 also include a central aperture sized to fit over drainage lumen connector 308, and a space or aperture, slot, or the like, (not shown) sized to fit or otherwise allow passage of inflation lumen extender 334. Proximal and distal tine deflectors 306 and 304 additionally include an aperture, space, or slot (not shown) sized to fit over or allow passage of bi-lumen tubing 321.

When assembled, distal tip 312 includes drainage aperture 328 to communicate with drainage lumen 326. A portion of distal tip 312 is preferably covered by connective sheath 314, to assist in connecting distal tip 312 to device 300 when assembled. Also, when assembled, connective sheath 314 preferably covers and encloses other componentry of device 300, including tine deflectors 306 and 304, tissue approximating structure 305 and 307, spacer 310, housing 340, and a distal portion of catheter shaft 302.

Balloon 316, upon assembly, is located at an exterior surface of device 300, in communication with an inflation lumen that is in communication with the proximal end of the device at port 319. The inflation lumen includes an inflation lumen of catheter shaft 302 (not shown) connected to a proximal end of inflation lumen extender 334, the distal end of which is connected to an inflation lumen (not shown) in distal tip 312, in communication with balloon 316.

The device, in addition to the foregoing, may also include other mechanisms or features, as will be appreciated by those of skill. As one example of a specific feature that may be incorporated into an embodiment of a device, an actuating mechanism or a portion of an actuating mechanism may be removable at an exterior portion of the device. For example, an actuating mechanism may extend through an elongate body of a device through an end or through a port at the proximal end of the device. The actuating mechanism or a portion thereof may be removably attached to the device and the tissue approximating structure, at the proximal end, so that a surgeon can operate the tissue approximating structure while the actuating mechanism is attached during a surgical procedure, and the actuating mechanism may be removed following the procedure to avoid inadvertent actuation by the patient during the healing period, during which the device is still installed in the patient. When the time comes to remove the device, the actuating mechanism may be re-attached externally to uninstall the device.

Figure 4:
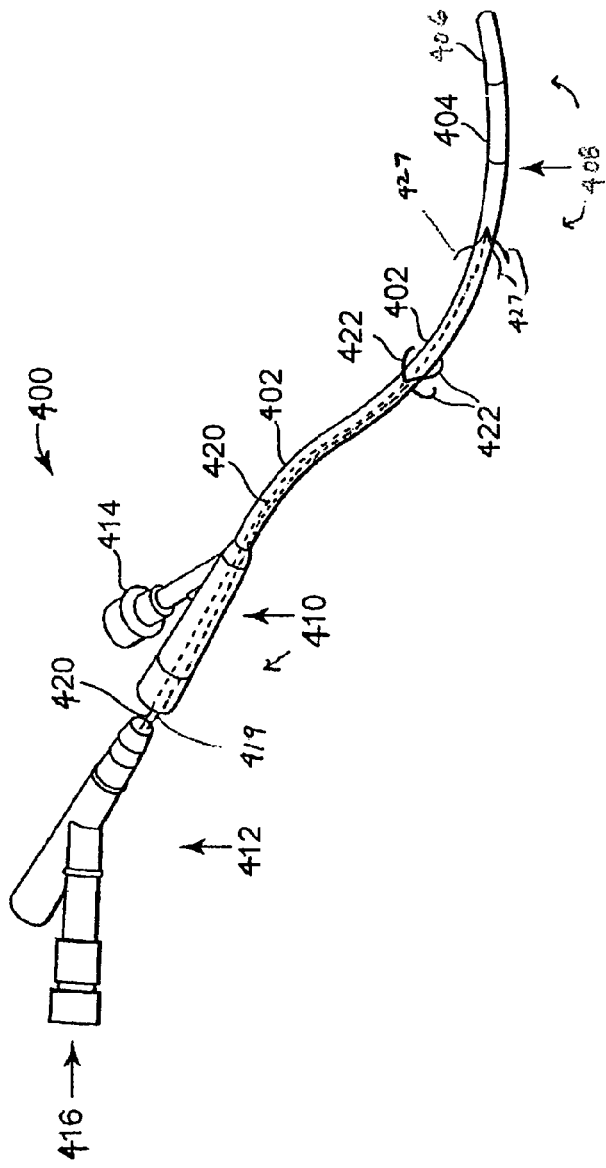
FIG. 4 is a perspective view of one embodiment of an anastomosis device of the invention.

FIG. 4 shows a single example of a modified-Foley-catheter-type anastomosis device according to the invention. Device 400 includes distal end 408, proximal end 401, attachment 412, elongate body 402, balloon 404, and drainage aperture 406. Tissue approximating structure of device 400 is shown as two sets of tines 422 and 427, which are connected to proximal end 410 by actuating mechanisms 419 and 420. The tines are included in the device using a design and related componentry and actuating mechanisms to allow a drainage lumen (not shown) of the device to remain open and unobstructed.

Still referring to FIG. 4, device 400 includes a port 414 near proximal end 410, and a receiving end that can be connected to attachment 412. Useful such proximal end and attachment configurations are well known, and such known or future developed proximal ends and attachments will be understood to be useful according to devices and methods of the invention. In the illustrated embodiment, proximal end 410 includes a port 414 that may connect to an inflation lumen (not shown) for inflating balloon 404. Another port, 416, part of attachment 412, can be used, e.g., with actuating mechanism 419 and 420. Attachment 412 may be attached to another portion of an actuating mechanism such as a turnable knob or a lever (not shown), etc., that can be moved or rotated to independently extend or retract tines 422 or 427. Other variations of these features of the illustrated attachment and proximal end will be understood by those of skill, and may be used in combination with the features of the present invention.

Figure 9:
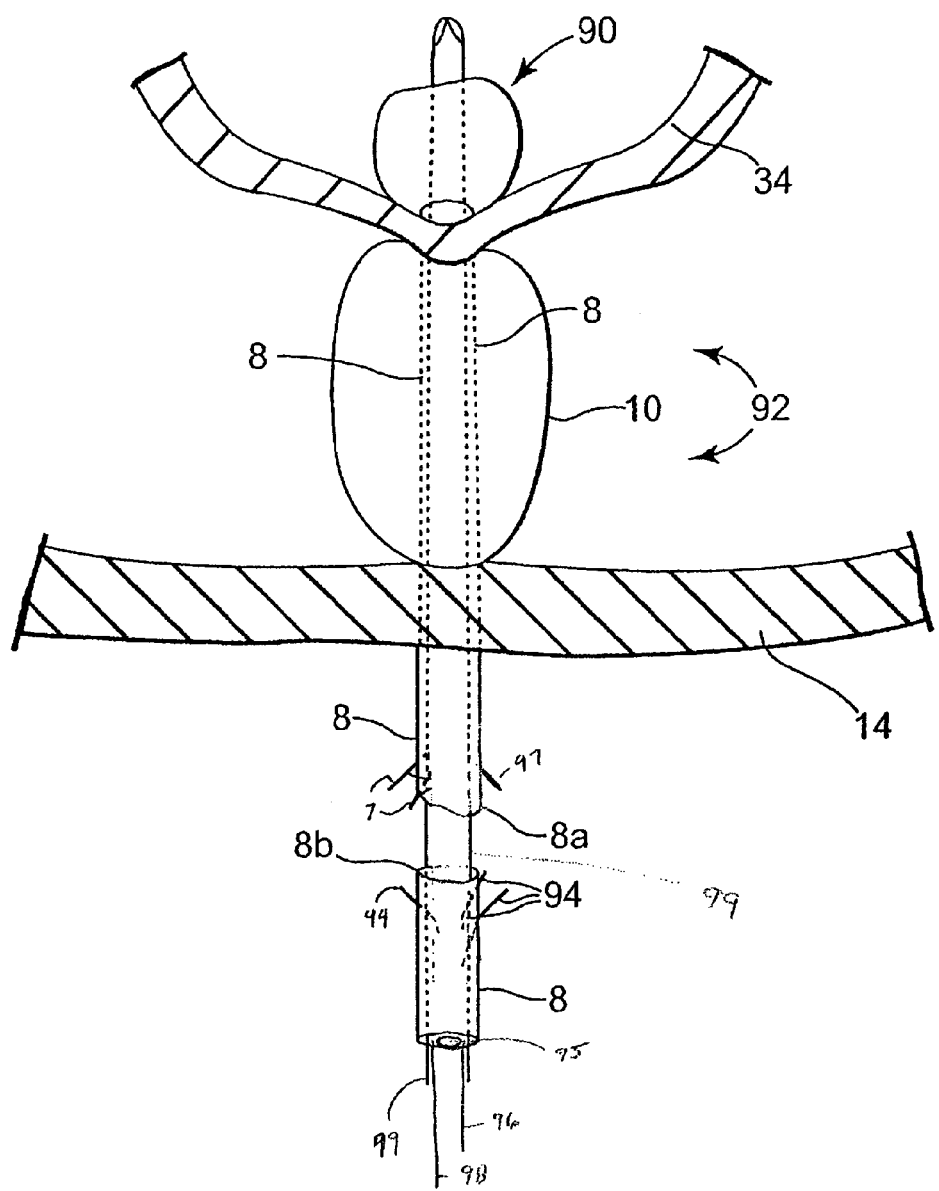
FIGS. 9 and 9a are partial cross-sectional views of two positions of an embodiment of an anastomosis device of the invention as used for securing two portions of a severed urethra.

According to specific methods of the invention, an anastomosis device includes tissue approximating structure that can be used to place or hold a cut or severed tissue or tissue surface in place for healing while the catheter is installed. Referring to FIG. 1, a radical prostatectomy procedure includes removal of the prostate 10 (indicated in dashes) and urethra 8 (also in dashes), leaving bladder 2 with bladder neck 4 having a severed tissue surface 6 at one end of removed urethra 8, and a urethral stump 12 extending from perineal floor 14, with urethral stump 12 having severed tissue surface 16 opposing the severed surface 6 of bladder neck 4. Referring to FIG. 9, an end-to-end urethral anastomosis procedure includes a step of severing the urethra 8, below perineal wall 14, to leave two opposing severed urethral tissues 8a and 8b. While the following description presents inventive devices and methods primarily in the context of vesico-urethral anastomosis relating to radical prostatectomy, it will be apparent that the invention can be applied to a variety of other procedures that require tissue approximation or other positioning of tissues relative to each other will benefit from devices as described herein, that include tissue approximating structure, and in particular where a fluid flow is also desired, such as drainage of urine.

Figure 2:
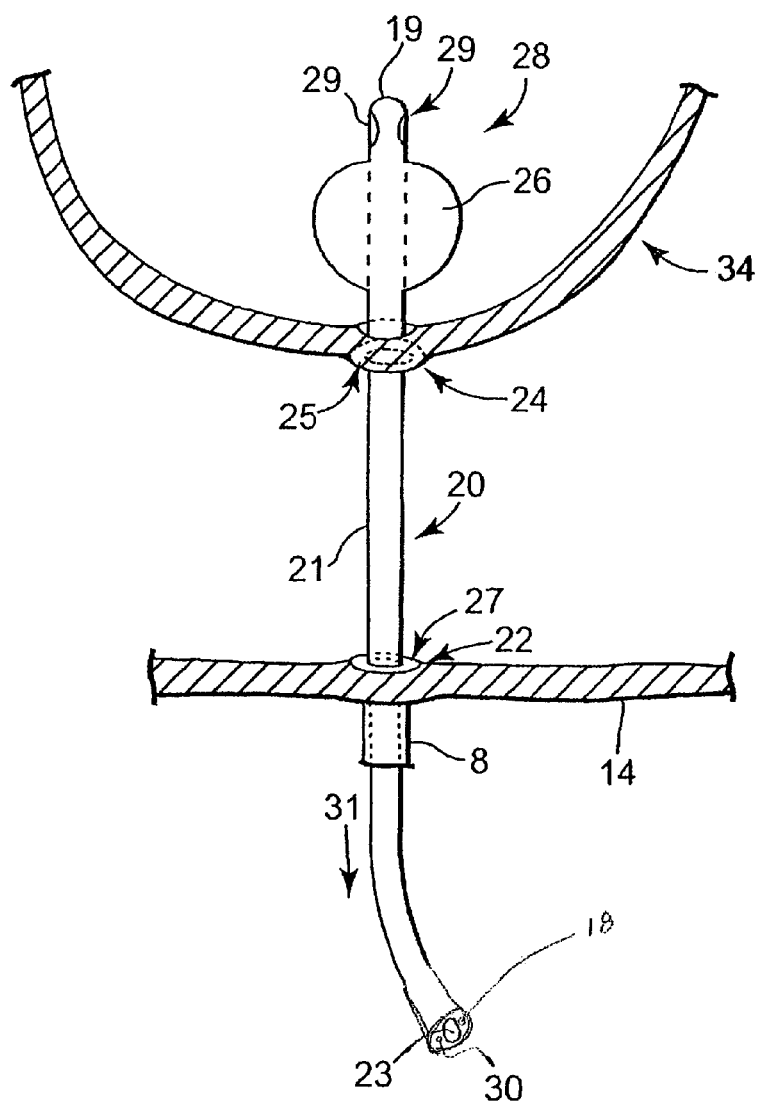
FIGS. 2 and 2a are partial cross-sectional views showing two positions of one embodiment of an anastomosis device according to the invention.
Figure 2A:
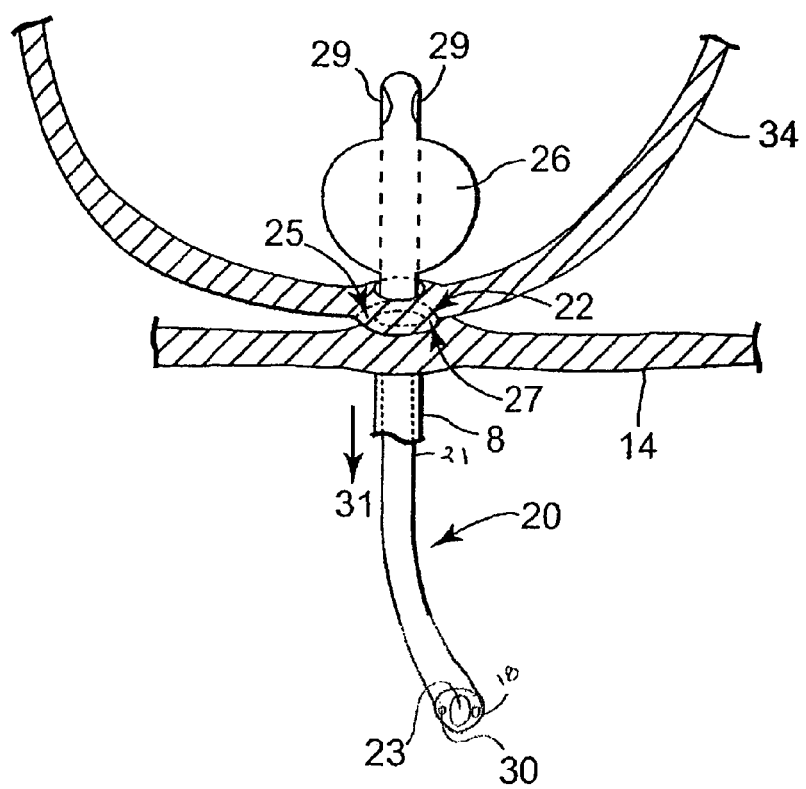

According to certain presently preferred embodiments of the invention, an anastomosis device may comprise a balloon located at the distal end of the device, for being positioned inside of the bladder during use. FIGS. 2 and 2a illustrate such an embodiment of an anastomosis device of the invention, installed for use within urethra 8 and bladder 34 following removal of a prostate (not shown).

Referring to FIG. 2, a prostate has been removed to leave a severed urethral stump 22 and opposing severed bladder neck 24. Anastomosis device 20 is installed through urethral stump 22 and bladder neck 24. The device 20 comprises an elongate body 21 and balloon 26 located at the distal end 28 of the device. Preferably and as shown, the device also includes drainage lumen 23 in communication with drainage apertures 29, located between the tip 19 of the distal end of the device 20 and balloon 26. Balloon 26 is inflated, after insertion into the bladder 34, by a flow of fluid through inflation lumen 30. Traction, as shown by arrow 31, can then be applied through the length of device 20. Referring to FIG. 2a, balloon 26 can be placed against the interior of the bladder 34 with the severed bladder neck tissue 25 in contact with severed urethral stump 22. The surface of severed bladder neck tissue 25 can be aligned with the surface 27 of severed urethral stump 22, around and along the axis of the elongate body 21, provided that no gap exists between the surfaces 25 and 27 of the respective severed tissues.

Figure 3:
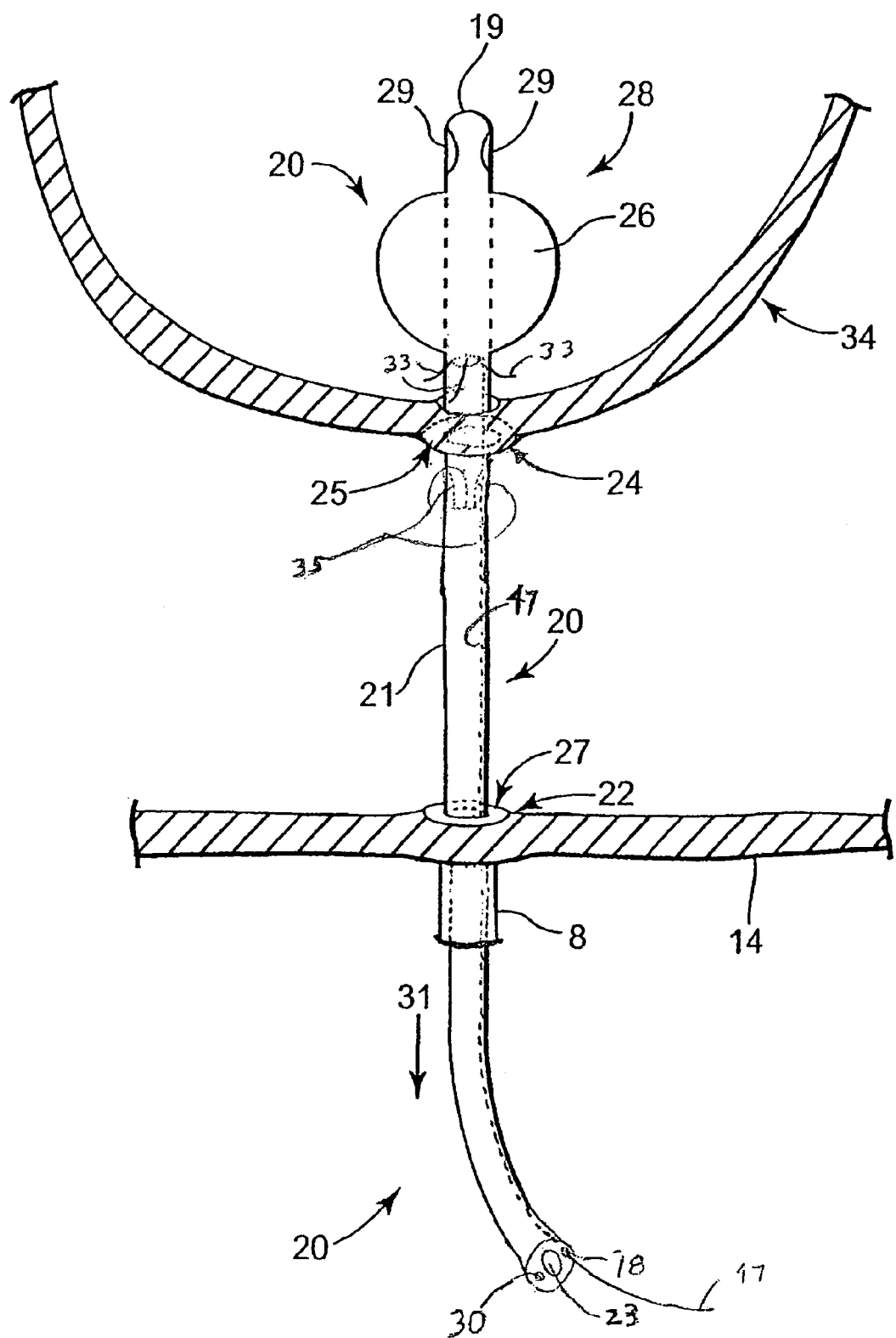
FIGS. 3 and 3a are partial cross-sectional views showing two positions of an embodiment of an anastomosis device according to the invention.
Figure 3A:
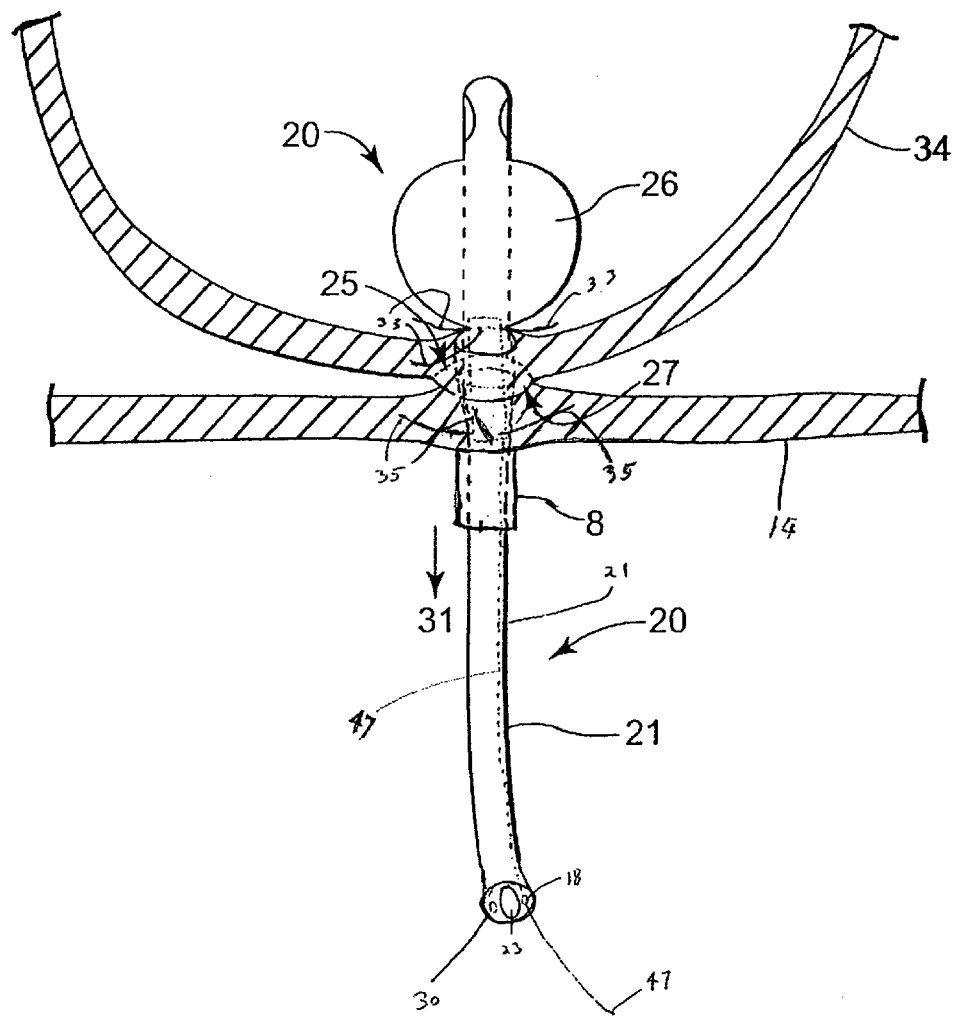

According to the invention, devices according to FIGS. 2 and 2a preferably include tissue approximating structure such as described herein, which structure or structures are not illustrated in these Figures for clarity of the drawings. However, FIGS. 3 and 3a show the configurations of FIGS. 2 and 2a, respectively, with the inclusion of illustrated tissue approximation structure. As an example, FIG. 3 shows tissue approximating structure located along the length of the elongate body 21, at a location that will place the tissue approximating structure near the urethral stump 22 or the perineal floor 14, for anastomosis. Such tissue approximating structure may include one or more sets of elongate metal tines. FIG. 3 shows two sets of tines, proximal tines 35 and distal tines 33. Proximal tines 35 are in a retracted position, and distal tines 33 are extended, as illustrated. Actuating mechanisms, in the form of wires or shafts, are illustrated as a single dashed line 47 extending from the tissue approximating structures to the proximal end of the device, through actuating lumen 18. Proximal tines 35 may extend from the elongate body 21 at a position (when installed, with the bladder drawn down to the perineal floor) below or proximal to the urethral stump 22 or perineal floor. Distal tines 33 can extend from body 21 at a location within bladder 34. Thus, in combination, extended distal tines 33 and extended proximal tines 35 can work together to maintain contact between urethral stump tissue 27 and bladder neck 24.

Referring still to FIG. 3, the prostate (not shown) has been removed to leave a severed urethral stump tissue 22 and opposing severed bladder neck 24. Anastomosis device 20 is installed through urethra 8, urethral stump 22, and bladder neck 24. The device 20 comprises balloon 26 located at distal end 28 of the device. The device also includes drainage lumen 23 in communication with drainage apertures 29. Balloon 26 is inflated and traction 31 applied through the length of device 20 to cause distal tines 33 and balloon 26 to contact the inside of bladder 34 (see FIG. 3a) while severed bladder neck tissue 25 contacts severed urethral stump tissue 27. As shown in FIG. 3a, the surface 25 of the severed bladder neck can be aligned with the surface 27 of the severed urethral stump, around and along the axis of device 20. Also shown in FIG. 3a are proximal tines 35 extended from elongated body 21 to contact and optionally penetrate into perineal floor 14 (optionally contacting or penetrating tissue below the perineal floor 14 such as the bulbar urethra 8). Distal tines 33 extend from body 21, into bladder 34, to contact an interior surface of bladder 34. Severed urethral stump tissue 27 contacts severed surface 25 of the bladder neck to allow healing and reconnection of the two severed tissue surfaces.

Generally, a specific method of the invention can include a step of performing a radical prostatectomy by a known or future developed technique, such as by a retropubic technique, a laparoscopic technique, or a transperineal technique. These techniques leave a bladder neck and a urethral stump for re-attachment. Prior techniques may use sutures or other mechanisms or structures that are separate from a catheter to re-attach the severed tissue. The use of sutures or other such separate mechanisms or structures is preferably not necessary and most preferably avoided according to methods of the invention.

The distal end of the anastomosis device of the present invention may optionally be partially installed during the prostatectomy procedure, e.g., up to the perineal floor, or may be installed to that point afterward. Following removal of the prostate, the distal end of the device is passed through the urethral stump and then through the bladder neck. From there, the technique can include inflating the balloon inside of the bladder, and using tissue approximating structure to hold the severed tissue surfaces of the urethral stump and the bladder neck into contact for healing. A preferred step can also be to close the bladder neck to a desired size via a purse-string suture.

Common to all vesico-urethral techniques can preferably be to carefully avoid damaging sensitive tissues near the bladder neck and urethral stump. Specifically, ureters are proximal to the bladder neck and should not be contacted. Proximal to the urethral stump are sensitive nerves and a sphincter. Some of these tissue structures are generally regarded as being at the 5 o'clock and 7 o'clock positions of the bladder neck and the urethral stump. Advantageously, devices and methods of the invention can afford significant opportunity to identify the location of these tissues, and position and reposition the tissue approximating structures to avoid them. As an additional feature of the device, markings can be made along a length of the outer surface of the catheter body, e.g., at the location where elongate tissue approximating structure extends from a body of a device. A surgeon can view these markings when positioning the body relative to a urethral stump and bladder neck, to avoid potential damage to sensitive tissue locations. Also in preferred embodiments, elongate tissue approximating structures such as tines or needles can be constructed and located to facilitate avoidance of sensitive tissues, such as by providing a set of three tines that radiate from a cross section of an elongate body at approximately 120 degree angles apart from each other.

FIG. 9 shows an additional embodiment of an inventive method and device relating to a urethral anastomosis procedure below the perineal floor. FIG. 9 illustrates device 90 having distal end 92 installed through perineal floor 14 and into bladder 34, through urethra 8 which passes through prostate 10. This procedure does not include removal of the prostate, but instead relates to severing and re-attaching urethra 8 at a point below perineal wall 14, e.g., re-attaching severed urethra portions 8a and 8b. According to the illustration, tines 94 and 97 can be used to hold surfaces of severed urethra portions 8a and 8b together for healing (see FIG. 9a). Specifically, proximal tines 94 and distal tines 97 are independently movable by actuating mechanisms 96 and 98, respectively, to retract or extend through elongate body 99. When installed, tines 94 and 97 are located along the body 99 at a location that allows each set of tines to contact a severed urethra tissue portion.

Figure 9A:
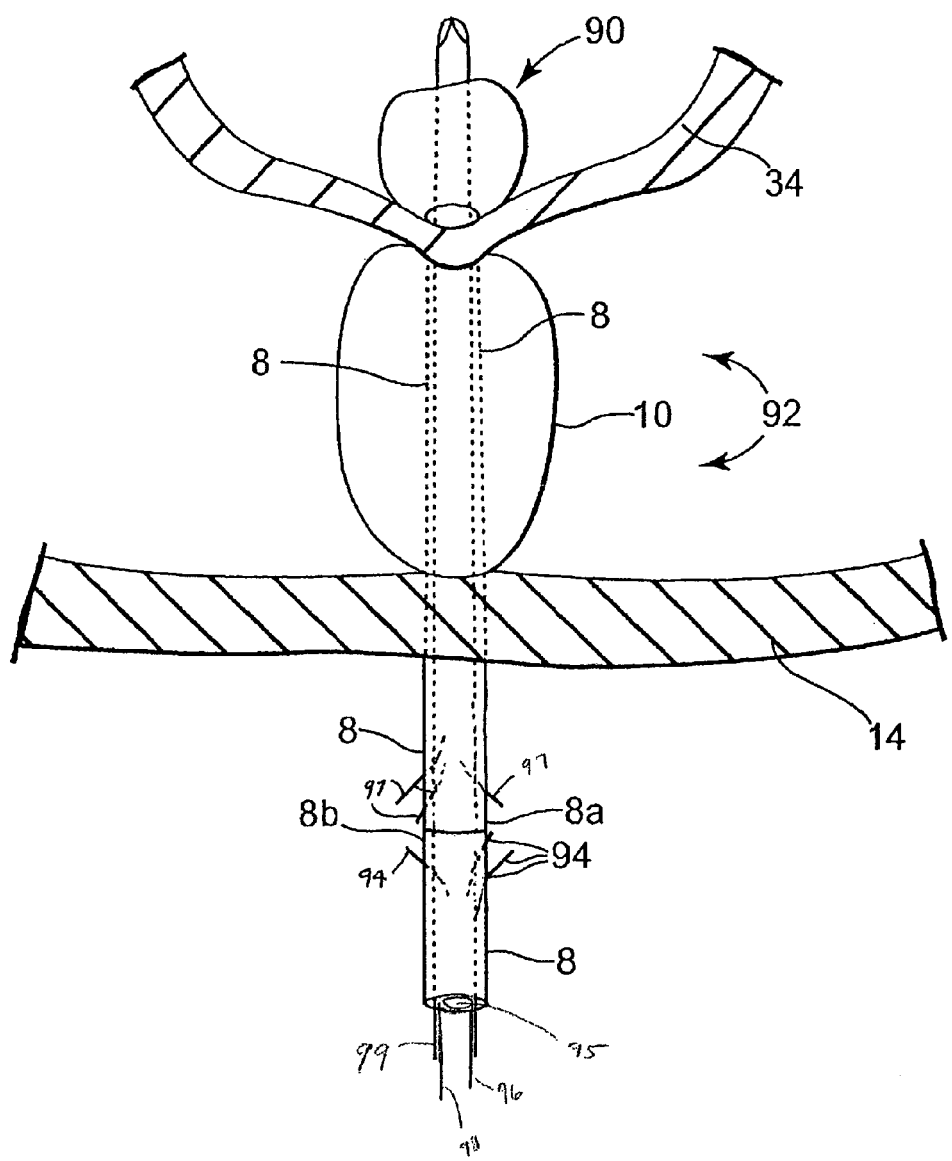

FIG. 9a illustrates the extended distal and proximal sets of tines 97 and 94 extending into opposing portions of severed urethra 8 and holding the severed tissue portions 8a and 8b in contact for healing. The installed device also includes a balloon in bladder 34 and an open drainage lumen that function together to cause urine to collect in the bladder and drain from the bladder through open central drainage lumen 95. Thus, the illustrated device may be left installed, including the tissue approximating structure, during the healing period. The open drainage lumen allows passage of bodily materials without clogging.

Figure 11:
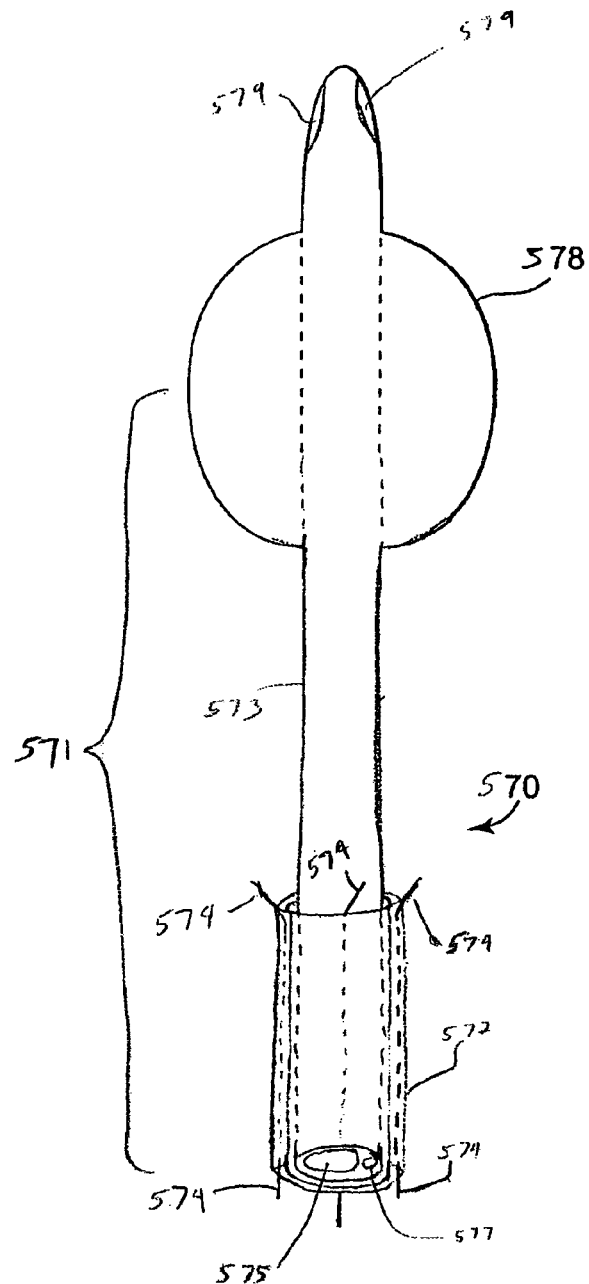
FIG. 11 is a front view of an embodiment of an anastomosis device according to the invention, including inner and outer elongate bodies.
Figure 11A:
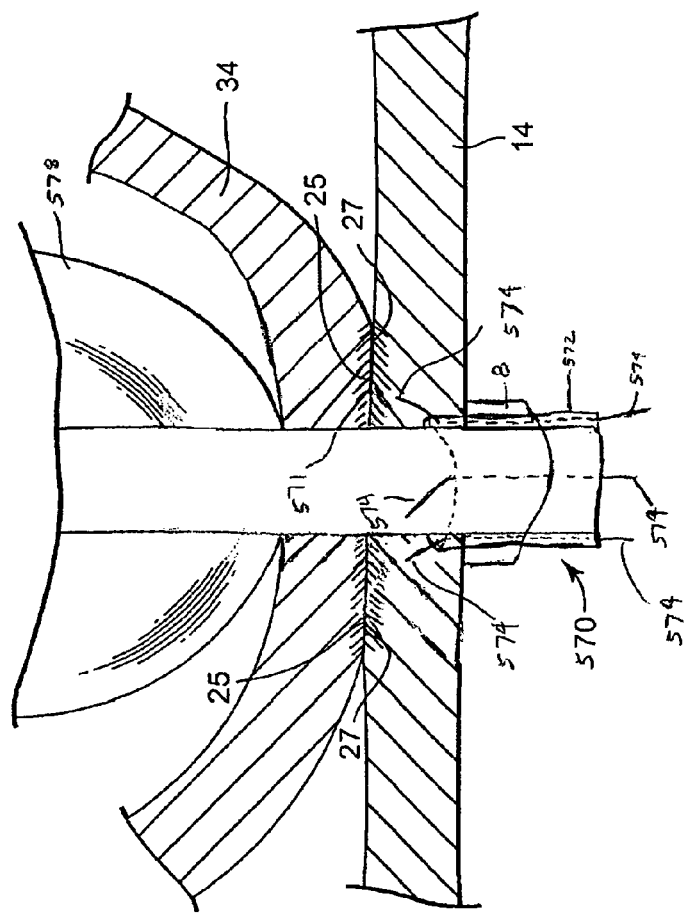
FIG. 11a is a partial cross-sectional view of the anastomosis device of FIG. 11 as used within a patient.

Still another embodiment of anastomosis device is shown in FIGS. 11 and 11a. This device, and details thereof, is discussed in Applicants' co-pending patent application, "ANASTOMOSIS DEVICE AND RELATED METHODS," AMS0008/US/2 filed on even date herewith, the entire contents of which are incorporated herein by reference. Device 570 includes a balloon 578, as well as elongate body 571 made up of inner elongate body 573 and outer elongate body 572. Outer elongate body 572 slides along inner elongate body 573 to allow positioning of outer elongate body 572 along a length of the inner elongate body 573. Drainage lumen 575, which is an open drainage lumen that does not contain components of tissue approximating structure or actuating mechanisms, extends from drainage apertures 579 to a proximal end of device 570. Inflation lumen 577 extends within a wall of inner body 573, from a proximal end of device 570 to balloon 578. Outer elongate body 572 includes tissue approximating structure that includes tines 574 that can be extended from a location at a distal end of outer elongate body 572. Each tine 574 extends within a channel (not shown) of the wall of outer elongate body 572, e.g., from that location to a proximal end of outer elongate body 572 and to a proximal end of device 570. Tines 574 can be extended and retracted from the their location at the distal end of outer elongate body 572 by an actuating mechanism (not shown) that connects to each tine 574 at the proximal end of device 570. Outer elongate body 572 extends to a proximal end of device 570, allowing outer elongate body 572 to be moved along a length of inner elongate body 573. As such, outer body 572 can be moved along a length of the elongate body 571, to position tissue approximating structure, tines 574, at different locations along the length of elongate body 571. Overall, tines 574 are positionable tissue approximating structure that can be positioned by movement of outer elongate body 572 along a length of elongate body 571. Once positioned as desired by movement of outer elongate body 572, tines 574 can be extended or retracted as desired, to contact, move, or hold tissue for healing. As desired, tines 574 can be extended either before or after contacting tissue, e.g., to hold tissue in place for healing, to manipulate tissue into position for healing, or both.

Referring to FIG. 11a, device 570 can be installed to locate balloon 578 inside of a bladder 34. Outer body 572 can be positioned, for example, along elongate body 571 to a location that will allow tines 574 to be extended from outer body 572 to contact tissue for healing, e.g., tissue of the perineal floor 14. Tines 574 can be extended or retracted either before or after perineal floor 14 is brought into contact with bladder 34. Thus, by combined movement of outer body 572 and actuation of tines 574, positionable tines 574 can be used to contact tissue of perineal floor 14 and bring the tissue into contact with tissue of bladder 34, to hold tissue of perineal floor 14 in contact with tissue of bladder 34, or to do both. The surface of severed bladder neck tissue 25 can be aligned with the surface 27 of severed urethral stump 22, around and along elongate body 71.

Figure 12:
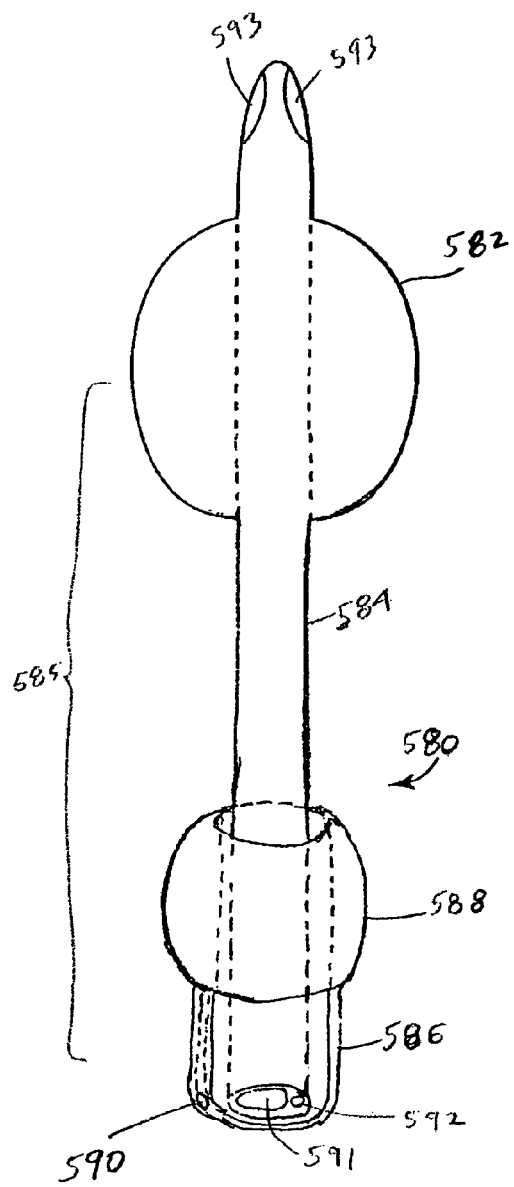
FIG. 12 is a front view of an embodiment of an anastomosis device according to the invention.
Figure 12A:
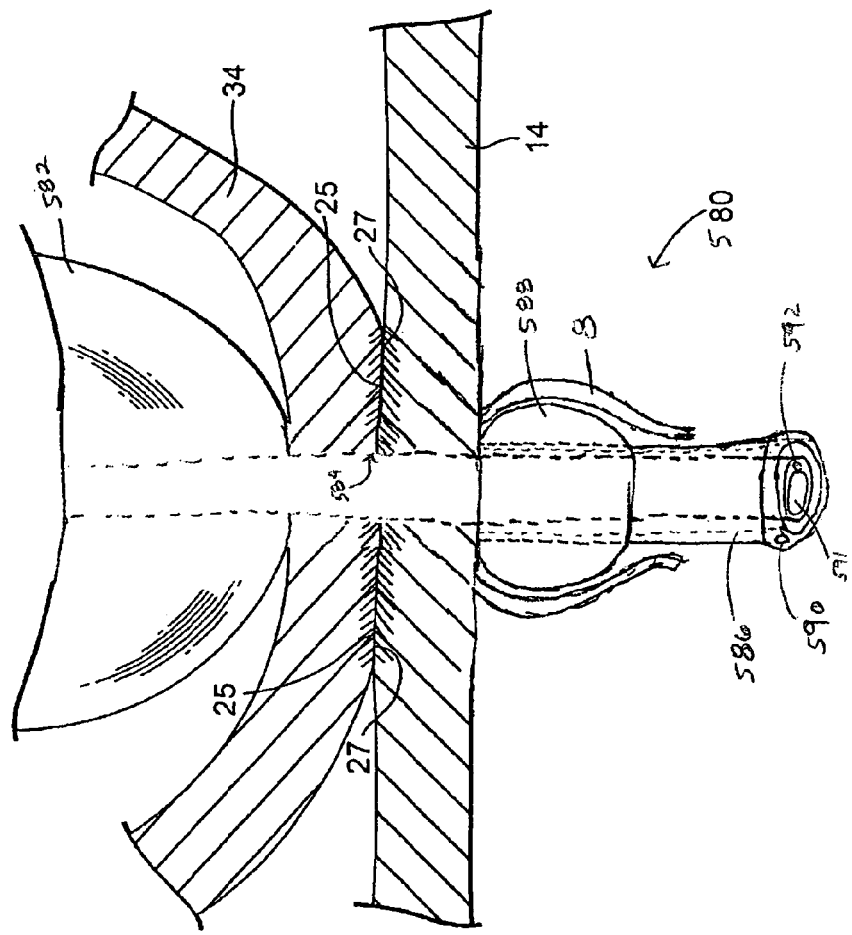
FIG. 12a is a partial cross-sectional view of the anastomosis device of FIG. 12 as used within a patient.

Still another embodiment of anastomosis device is shown in FIGS. 12 and 12a. This device, and details thereof, is discussed in Applicants' co-pending patent application, "ANASTOMOSIS DEVICE AND RELATED METHODS," AMS0008/US/2 filed on even date herewith. Device 580 includes a balloon 582, inner elongate body 584, and outer elongate body 586, which together make up elongate body 585. Drainage lumen 591, which is an open drainage lumen that does not contain any components of tissue approximating structure or actuating mechanisms, extends from drainage apertures 593 to a proximal end of device 580. Inflation lumen 592 extends within a wall of inner body 584, from a proximal end of device 580 to balloon 582. Outer elongate body 586 includes balloon 588, which functions as tissue approximating structure. Balloon 588 communicates through lumen 590 within the wall of outer elongate body 586, e.g., extending from balloon 588 to a proximal end of outer elongate body 586 and to a proximal end of device 580. Balloon 588 can be inflated and deflated to extend from the distal end of outer elongate body 586 by flow of fluid through inflation lumen 590. Outer elongate body 586 extends to a proximal end of device 580, allowing outer elongate body 586 to be moved along a length of inner elongate body 584. As such, outer elongate body 586 can be moved along a length of body 584 to position balloon 88 at different locations along a length of elongate body 585. Once positioned as desired by movement of outer elongate body 586, balloon 588 can be extended or retracted as desired, to contact, move, or hold tissue for healing. As desired, balloon 588 can be extended either before or after tissue is moved into place during an anastomosis procedure.

Referring to FIG. 12a, device 580 can be installed to locate balloon 582 inside of a bladder 34. Tissue of perineal floor 14 can be positioned to contact tissue of bladder 34, by movement of perineal floor 14 along elongate body 584. The surface of severed bladder neck tissue 25 can be aligned with the surface 27 of severed urethral stump 22, around and along elongate body 584. Balloon 588 can be inflated at a desired time during the procedure relative to movement of perineal floor 14 to contact bladder 34. Thus, by combined movement of outer body 586 and inflation of balloon 588, tissue approximating structure balloon 588 can be used to contact tissue of perineal floor 14 and bring the tissue into contact with tissue of bladder 34, to hold tissue of perineal floor 14 in contact with tissue of bladder 34, or to do both.

Any of the various embodiments of an anastomosis device as described herein can remain installed in the patient during the time required for healing or partial healing of the two tissue surfaces together, during which time the balloon preferably remains inflated to prevent urine from passing through the bladder neck. The healing period can be considered the time period taken for severed tissue to achieve a water tight anastomosis. The healing period can depend on many factors such as the type of operation and the patient, and can take, e.g., from possibly as little as one or two days, up to possibly two months, with periods of from one to four weeks being sometimes typical. After the desired healing period has occurred, the anastomosis device may be removed. Such removal of the device preferably includes disengaging at least a portion of the tissue approximation structures that are engaged with tissue of the patient before removal of the device.

Following is one exemplary series of more detailed steps useful according to the methods of the invention, for using an inventive anastomosis device to perform a prostatectomy.

1. Perform a radical prostatectomy by any method such as retropubic, laparoscopic, or transperineal, until prior to the vesico-urethral anastomosis. The following description is in the context of a retropubic radical prostatectomy, and with reference to an embodiment of the inventive device as illustrated at FIGS. 3 and 3a, for example.
2. Optionally close the bladder neck to the desired size via a purse-string suture.

3. The anastomosis device (AD) can be inserted into the bladder prior to the suturing to help determine the desired size of the bladder neck, or the bladder can be sutured independently.
4. Insert the AD through the meatus until it exits the urethral stump in the open abdomen.
5. Pull the AD until enough length has been exposed to reach the bladder.
6. Insert the AD into the bladder and inflate the balloon.
7. Extend the top (distal) tines of the AD and visually ensure that the tines do not penetrate the ureters of the bladder. This can be facilitated by extending and retracting the tines and seeing the "bump" form on the exterior wall of the bladder. The AD may also have visual markers on the external wall of the AD proximal to the top tines to mark the location of the tines.
8. The bladder can then be lowered to the perineal floor by releasing the traction on the bladder and physically moving the bladder down by hand while lightly maintaining tension on the AD.
9. Once the bladder has been drawn to contact the urethral stump, a light tension can be placed on the AD while the proximal tines are extended into the perineal floor by actuating means.
10. The bladder can then be filled with water or saline using the drainage port on the AD and the anastomosis site can be checked for leaks.
11. If a leak is experienced the AD can be repositioned until the desired performance is reached.
12. The AD can remain in place for a time depending on the healing needs of the individual patient.
13. Remove the AD after an appropriate healing time has elapsed.

The steps presented above are meant to illustrate one exemplary procedure for a particular type of surgery; however, it is understood that similar steps may be used for different surgeries or procedures that may include more, less, or different steps that will be specific to each type of surgery. The steps for the above described surgery, or any other surgeries that use the devices and methods of the present invention, may occur in a different order and may be repeated or omitted, depending on the patient.

The invention claimed is:

1. An anastomosis device comprising:
an elongate body comprising a proximal end, a distal end, and an open drainage lumen extending through at least a portion of a length of the elongate body,
a drainage aperture at a distal end of the elongate body for communication with the proximal end of the elongate body through the drainage lumen, wherein the open drainage lumen comprises an unobstructed passage from the proximal end of the elongate body to the drainage aperture,
a balloon spaced from the drainage aperture along the length of the elongate body, and
at least one elongate distal tissue approximating structure at the distal end of the elongate body and outwardly extendable from the elongate body on a proximal side of the balloon along the length of the elongate body so that a distal end of each distal elongate tissue approximating structure is spaced from the elongate body;
at least one elongate proximal tissue approximating structure, each of which is outwardly extendable from the elongate body on a proximal side of the at least one elongate distal tissue approximating structure so that a distal end of each proximal elongate tissue approximating structure is spaced from the elongate body; and
a tine support comprising a tine support body that includes a hollow channel and a tine deflector, wherein at least one of the at least one elongate distal tissue approximating structure and the at least one elongate proximal tissue approximating structure comprises:
a tine frame slidably supported by a drainage lumen connector that extends along at least a portion of the length of the elongate body,
at least one tine extending from the tine frame, each tine supported by an aperture of the tine deflector, and
an actuating mechanism operably connecting the tine frame to the proximal end of the device through an actuating lumen that extends along at least a portion of the length of the elongate body.

2. An anastomosis device comprising:
an elongate body comprising a proximal end, a distal end, and an open drainage lumen extending through at least a portion of a length of the elongate body,
a drainage aperture at a distal end of the elongate body for communication with the proximal end of the elongate body through the drainage lumen, wherein the open drainage lumen comprises an unobstructed passage from the proximal end of the elongate body to the drainage aperture,
a balloon spaced from the drainage aperture along the length of the elongate body, and
at least one elongate distal tissue approximating structure at the distal end of the elongate body and outwardly extendable from the elongate body on a proximal side of the balloon along the length of the elongate body so that a distal end of each distal elongate tissue approximating structure is spaced from the elongate body; and
at least one elongate proximal tissue approximating structure, each of which is outwardly extendable from the elongate body on a proximal side of the at least one elongate distal tissue approximating structure so that a distal end of each proximal elongate tissue approximating structure is spaced from the elongate body,
wherein the elongate body further comprises a body wall comprising an inflation lumen extending along the length of the elongate body from the proximal end to the balloon, and wherein the at least one elongate distal tissue approximating structure and the at least one elongate proximal tissue approximating structure comprise extendable tines.

3. The device of claim 2, wherein the device is installable in a body with the balloon positionable in a bladder so that the at least one elongate distal tissue approximating structure and the at least one elongate proximal tissue approximating structure are capable of contacting at least one tissue structure adjacent to the bladder.

4. The device of claim 2, the elongate body further comprising a catheter shaft having a substantially solid wall, wherein the open drainage lumen is defined by an interior surface of the wall of the catheter shaft.

5. The device of claim 2, wherein the distal and proximal tissue approximating structures can be extended from and retracted into the elongate body.

6. The device of claim 2, wherein the passage from the proximal end of the elongate body to the drainage aperture comprises a port at the proximal end of the elongate body, wherein the port is in communication with the drainage lumen.

7. The device of claim 2, wherein the drainage lumen comprises a port at the proximal end of the elongate body.

8. An anastomosis device comprising:
an elongate body comprising a proximal end, a distal end, and an open drainage lumen extending through at least a portion of a length of the elongate body,
a drainage aperture at a distal end of the elongate body for communication with the proximal end of the elongate body through the drainage lumen, wherein the open drainage lumen comprises an unobstructed passage from the proximal end of the elongate body to the drainage aperture,
a balloon spaced from the drainage aperture along the length of the elongate body, and
at least one elongate distal tissue approximating structure at the distal end of the elongate body and outwardly extendable from the elongate body on a proximal side of the balloon along the length of the elongate body so that a distal end of each distal elongate tissue approximating structure is spaced from the elongate body; and
at least one elongate proximal tissue approximating structure, each of which is outwardly extendable from the elongate body on a proximal side of the at least one elongate distal tissue approximating structure so that a distal end of each proximal elongate tissue approximating structure is spaced from the elongate body,
wherein the at least one elongate distal tissue approximating structure comprises at least one distal elongate tine positioned to extend from the elongate body on the proximal side of the balloon, and the at least one elongate proximal tissue approximating structure comprises at least one proximal elongate tine positioned to extend from the elongate body on a proximal side of the at least one elongate distal tissue approximating structure.

9. The device of claim 8, wherein at least one of the at least one elongate distal tissue approximating structure and the at least one elongate proximal tissue approximating structure further comprises an actuating mechanism.

10. The device of claim 9, wherein the actuating mechanism comprises a wire.

11. The device of claim 8 comprising
a proximal tine deflector comprising a body that includes at least one arcuate aperture,
a distal tine deflector comprising a body that includes at least one aperture,
wherein the at least one elongate distal tissue approximating structure comprises:
a distal tine frame slidably supported by a drainage lumen connector, wherein the at least one distal elongate tine extends from the distal tine frame, each distal tine movably supported by the at least one aperture of the distal tine deflector,
a distal actuating mechanism operably connecting the distal tine frame to the proximal end of the device through an actuating lumen that extends along at least a portion of the elongate body, and wherein
the at least one elongate proximal tissue approximating structure comprises
a proximal tine frame slidably supported by a drainage lumen connector wherein the at least one proximal tine extends from the proximal tine frame, each proximal tine movably supported by the at least one aperture of the proximal tine deflector,
a proximal actuating mechanism operably connecting the proximal tine frame to the proximal end of the device through the actuating lumen.

12. The device of claim 11, wherein the at least one elongate distal tissue approximating structure and the at least one elongate proximal tissue approximating structure are positionable within a body for contacting adjacent tissue structures.

13. An anastomosis device comprising
an elongate body having a body wall, a proximal end, and a distal end, a drainage aperture at the distal end,
a drainage lumen extending along at least a portion of a length of the elongate body and connecting the drainage aperture to the proximal end,
an inflatable balloon spaced proximally from the drainage aperture along the length of the elongate body,
an inflation lumen extending within a length of the body wall, connecting the balloon to the proximal end,
a distal tissue approximating structure comprising at least one distal tine connected to a distal frame, each distal tine extendably supported within an aperture of a distal tine deflector,
a distal actuating mechanism operably connecting the distal frame to the proximal end of the device, through an actuating lumen extending along a length of the elongate body in the body wall,
a proximal tissue approximating structure comprising at least one proximal tine connected to a proximal frame, each proximal tine extendably supported within an aperture of a proximal tine deflector,
a proximal actuating mechanism operably connecting the proximal frame to the proximal end of the device, through the actuating lumen.

14. The device of claim 13 wherein the distal frame and the proximal frame are cylindrical.

15. The device of claim 13 wherein
the distal tine deflector comprises one or more aperture located within the body wall at a location along a length of the body wall on a proximal side of the drainage aperture, and the distal tissue approximating structure can be extended and retracted from the body wall through the one or more apertures, and
the proximal tine deflector comprises one or more aperture located within the body wall at a location along a length of the body wall on a proximal side of the drainage aperture, and the proximal tissue approximating structure can be extended and retracted from the body wall through the one or more aperture.

16. An anastomosis device comprising
an elongate body having a body wall, a proximal end, and a distal end, and an open drainage lumen extending through at least a portion of a length of the elongate body, the open drainage lumen comprising an unobstructed passage from the proximal end of the elongate body to the drainage aperture,
a drainage aperture at the distal end,
an inflatable balloon located on a proximal side of the drainage aperture along the length of the elongate body,
an inflation lumen extending within a length of the body wall, connecting the balloon to the proximal end,
a distal tissue approximating structure at the distal end of the elongate body and comprising at least one distal tine connected to a distal frame, each distal tine extending through an aperture located within the body wall at a location along a length of the body wall on a proximal side of the drainage aperture, and each distal tine being capable of extending from and retracting into the body wall through the aperture,
a distal actuating mechanism operably connecting the distal frame to the proximal end of the device through an actuating lumen extending along a length of the elongate body in the body wall, a proximal tissue approximating structure at the distal end of the elongate body and comprising at least one proximal tine connected to a proximal frame, each proximal tine extending through another aperture located within the body wall at a location along a length of the body wall on a proximal side of the drainage aperture, and each proximal tine being capable of extending from and retracting into the body wall through the aperture, a proximal actuating mechanism operably connecting the proximal frame to the proximal end of the device, through the actuating lumen.

17. The device of claim 16 wherein the distal frame and the proximal frame are cylindrical.

\* \* \* \* \*